(12) United States Patent
Jackson et al.

(10) Patent No.: US 10,543,021 B2
(45) Date of Patent: Jan. 28, 2020

(54) PIVOTAL BONE ANCHOR ASSEMBLY HAVING AN OPEN RING POSITIONER FOR A RETAINER

(71) Applicant: Roger P. Jackson, Praire Village, KS (US)

(72) Inventors: Roger P. Jackson, Prairie Village, KS (US); James L. Surber, Kansas City, KS (US)

(73) Assignee: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 15/897,486

(22) Filed: Feb. 15, 2018

(65) Prior Publication Data

US 2018/0168697 A1    Jun. 21, 2018

Related U.S. Application Data

(63) Continuation of application No. 15/629,709, filed on Jun. 21, 2017, now Pat. No. 9,924,975, which is a continuation-in-part of application No. 15/521,163, filed as application No. PCT/US2015/056706 on Oct. 21, 2015, now Pat. No. 10,188,432.

(60) Provisional application No. 62/352,876, filed on Jun. 21, 2016, provisional application No. 62/362,830, filed on Jul. 15, 2016, provisional application No.
(Continued)

(51) Int. Cl.
*A61B 17/70* (2006.01)
*A61B 17/86* (2006.01)

(52) U.S. Cl.
CPC ...... *A61B 17/7037* (2013.01); *A61B 17/7038* (2013.01); *A61B 17/8605* (2013.01); *A61B 17/864* (2013.01)

(58) Field of Classification Search
CPC .............. A61B 17/7037; A61B 17/702; A61B 17/7019; A61B 17/7026; A61B 17/7022; A61B 17/7034; A61B 17/7031; A61B 17/7035; A61B 17/7032; A61B 17/7038; A61B 17/8605; A61B 17/864
USPC .................................. 606/246–279, 300–328
See application file for complete search history.

(56) References Cited

U.S. PATENT DOCUMENTS

| 5,501,684 A | 3/1996 | Schlapfer |
| 5,672,176 A | 9/1997 | Biedermann et al. |

(Continued)

FOREIGN PATENT DOCUMENTS

WO    WO 2005/018471    3/2005

OTHER PUBLICATIONS

Extended European Search Report, EP 15852384.5, dated Jun. 22, 2018.

*Primary Examiner* — Pedro Philogene
(74) *Attorney, Agent, or Firm* — Polsinelli PC

(57) ABSTRACT

A pivotal bone anchor assembly includes a shank sub-assembly comprising a shank and a coupler, and a receiver sub-assembly comprising a receiver having a bore with a bottom opening and a snap-fit assembly proximate the bottom opening comprising an insert, a retainer ring positioned within an expansion chamber, and a positioner configured to hold the retainer ring in position. The shank sub-assembly is uploaded through the receiver bottom opening such that the positioner is pushed up into a holder chamber and the retainer rings engages a circumferential locking groove of the coupler to secure the shank sub-assembly with the receiver sub-assembly with a snap-fit connection.

32 Claims, 25 Drawing Sheets

Related U.S. Application Data

62/212,253, filed on Aug. 31, 2015, provisional application No. 62/200,501, filed on Aug. 3, 2015, provisional application No. 62/200,491, filed on Aug. 3, 2015, provisional application No. 62/194,955, filed on Jul. 21, 2015, provisional application No. 62/137,707, filed on Mar. 24, 2015, provisional application No. 62/137,713, filed on Mar. 24, 2015, provisional application No. 62/078,173, filed on Nov. 11, 2014, provisional application No. 62/078,154, filed on Nov. 11, 2014, provisional application No. 62/066,813, filed on Oct. 21, 2014, provisional application No. 62/066,806, filed on Oct. 21, 2014.

(56) References Cited

U.S. PATENT DOCUMENTS

| | | | |
|---|---|---|---|
| 5,735,853 A | 4/1998 | Olerud | |
| 5,891,145 A | 4/1999 | Morrison et al. | |
| 6,063,090 A | 5/2000 | Schlapfer | |
| 6,146,383 A | 11/2000 | Studer et al. | |
| 6,241,731 B1 | 6/2001 | Fiz | |
| 6,280,442 B1 | 8/2001 | Barker et al. | |
| 6,626,908 B2 | 9/2003 | Cooper et al. | |
| 6,648,888 B1 | 11/2003 | Shluzas | |
| 6,660,004 B2 * | 12/2003 | Barker | A61B 17/7037 606/266 |
| 6,716,214 B1 | 4/2004 | Jackson | |
| 6,740,086 B2 | 5/2004 | Richelsoph | |
| 6,837,889 B2 | 1/2005 | Shluzas | |
| 7,001,389 B1 | 2/2006 | Navarro et al. | |
| 7,066,937 B2 | 6/2006 | Shluzas | |
| 7,160,300 B2 | 1/2007 | Jackson | |
| 7,179,261 B2 | 2/2007 | Sicvol et al. | |
| 7,186,255 B2 | 3/2007 | Baynham | |
| 7,306,606 B2 | 12/2007 | Sasing | |
| 7,322,981 B2 | 1/2008 | Jackson | |
| 7,491,218 B2 | 2/2009 | Landry et al. | |
| 7,530,992 B2 | 5/2009 | Biedermann et al. | |
| 7,618,444 B2 | 11/2009 | Shluzas | |
| 7,625,396 B2 | 12/2009 | Jackson | |
| 7,766,945 B2 | 8/2010 | Nilsson et al. | |
| 7,776,067 B2 | 8/2010 | Jackson | |
| 7,833,251 B1 | 11/2010 | Ahlgren et al. | |
| 7,857,834 B2 | 12/2010 | Boschert | |
| 7,875,065 B2 | 1/2011 | Jackson | |
| 7,922,748 B2 | 4/2011 | Hoffman | |
| 7,947,065 B2 | 5/2011 | Hammill et al. | |
| 8,021,397 B2 | 9/2011 | Farris et al. | |
| 8,034,089 B2 | 10/2011 | Matthis et al. | |
| 8,048,112 B2 | 11/2011 | Suziki et al. | |
| 8,048,126 B2 | 11/2011 | Altarac et al. | |
| 8,066,744 B2 | 11/2011 | Justis et al. | |
| 8,075,599 B2 * | 12/2011 | Johnson | A61B 17/7032 606/246 |
| 8,133,262 B2 * | 3/2012 | Whipple | A61B 17/7037 606/265 |
| 8,137,386 B2 | 3/2012 | Jackson | |
| 8,206,422 B2 | 6/2012 | Hestad et al. | |
| 8,277,485 B2 | 10/2012 | Krishna et al. | |
| 8,361,129 B2 | 1/2013 | Chao | |
| 8,430,914 B2 | 4/2013 | Spratt et al. | |
| 8,444,681 B2 | 5/2013 | Jackson et al. | |
| 8,449,578 B2 | 5/2013 | Keiser et al. | |
| 8,506,609 B2 | 8/2013 | Biedermann et al. | |
| 8,591,558 B2 | 11/2013 | Matthis et al. | |
| 8,636,778 B2 * | 1/2014 | Gephart | A61B 17/7037 606/267 |
| 8,771,324 B2 | 7/2014 | Black | |
| 8,814,913 B2 | 8/2014 | Jackson | |
| 8,986,349 B1 | 3/2015 | German | |
| 9,168,069 B2 | 10/2015 | Jackson | |
| 9,254,150 B2 | 2/2016 | Biedermann et al. | |
| 9,439,681 B2 | 9/2016 | Keyer et al. | |
| 9,456,853 B2 | 10/2016 | Jackson | |
| 9,526,529 B2 | 12/2016 | Charvet | |
| 9,648,134 B2 | 5/2017 | Hannen | |
| 9,724,130 B2 | 8/2017 | Chandanson et al. | |
| 9,895,170 B2 | 2/2018 | Biedermann et al. | |
| 9,895,172 B2 | 2/2018 | Biedermann et al. | |
| 9,918,745 B2 | 3/2018 | Jackson | |
| 9,924,971 B2 | 3/2018 | Biedermann et al. | |
| 9,924,975 B2 * | 3/2018 | Jackson | A61B 17/7037 |
| 9,980,753 B2 | 5/2018 | Jackson | |
| 10,039,572 B2 | 8/2018 | Harris et al. | |
| 10,188,432 B2 | 1/2019 | Jackson | |
| 2002/0022842 A1 | 2/2002 | Horvath et al. | |
| 2002/0026193 A1 | 2/2002 | Barker et al. | |
| 2002/0143341 A1 | 10/2002 | Biedermann et al. | |
| 2004/0039383 A1 | 2/2004 | Jackson | |
| 2004/0049196 A1 | 3/2004 | Jackson | |
| 2004/0167526 A1 | 8/2004 | Jackson | |
| 2004/0267264 A1 | 12/2004 | Konieczynski et al. | |
| 2005/0080415 A1 | 4/2005 | Keyer et al. | |
| 2005/0187548 A1 | 8/2005 | Butler et al. | |
| 2005/0261687 A1 | 11/2005 | Garamszegi | |
| 2006/0025771 A1 | 2/2006 | Jackson | |
| 2006/0058788 A1 | 3/2006 | Hammer | |
| 2006/0155277 A1 | 7/2006 | Metz-Stavenhagen | |
| 2006/0200131 A1 | 9/2006 | Chao et al. | |
| 2007/0088357 A1 | 4/2007 | Johnson et al. | |
| 2007/0090238 A1 | 4/2007 | Justis | |
| 2007/0093826 A1 | 4/2007 | Hawkes et al. | |
| 2007/0093827 A1 | 4/2007 | Warnick | |
| 2007/0118117 A1 | 5/2007 | Altarac et al. | |
| 2007/0118123 A1 | 5/2007 | Strausbaugh et al. | |
| 2007/0123862 A1 | 5/2007 | Warnick | |
| 2007/0233087 A1 | 10/2007 | Schlapfer | |
| 2007/0270813 A1 | 11/2007 | Garamszegi | |
| 2007/0270831 A1 | 11/2007 | Dewey et al. | |
| 2008/0132957 A1 | 6/2008 | Matthis et al. | |
| 2008/0140135 A1 | 6/2008 | Konieczynski et al. | |
| 2008/0140136 A1 | 6/2008 | Jackson | |
| 2008/0147129 A1 | 6/2008 | Biedermann et al. | |
| 2008/0154315 A1 | 6/2008 | Jackson | |
| 2008/0161863 A1 | 7/2008 | Arnold et al. | |
| 2008/0215100 A1 | 9/2008 | Matthis et al. | |
| 2008/0234761 A1 | 9/2008 | Jackson | |
| 2008/0269809 A1 | 10/2008 | Garamszegi | |
| 2008/0294202 A1 | 11/2008 | Peterson et al. | |
| 2008/0319490 A1 | 12/2008 | Jackson | |
| 2009/0012567 A1 | 1/2009 | Biedermann et al. | |
| 2009/0062865 A1 | 3/2009 | Schumacher | |
| 2009/0062866 A1 | 3/2009 | Jackson | |
| 2009/0062867 A1 | 3/2009 | Schumacher | |
| 2009/0069852 A1 | 3/2009 | Farris et al. | |
| 2009/0069853 A1 | 3/2009 | Schumacher | |
| 2009/0105769 A1 | 4/2009 | Rock et al. | |
| 2009/0105770 A1 | 4/2009 | Berrevoets et al. | |
| 2009/0204155 A1 | 8/2009 | Aschmann | |
| 2009/0240290 A1 | 9/2009 | Choi | |
| 2010/0004692 A1 | 1/2010 | Biedermann | |
| 2010/0023061 A1 | 1/2010 | Randol et al. | |
| 2010/0094343 A1 | 4/2010 | Pham et al. | |
| 2010/0094349 A1 | 4/2010 | Hammer et al. | |
| 2010/0100137 A1 | 4/2010 | Justis et al. | |
| 2010/0114170 A1 | 5/2010 | Barrus et al. | |
| 2010/0152787 A1 | 6/2010 | Walsh et al. | |
| 2010/0198272 A1 | 8/2010 | Keyer et al. | |
| 2010/0234902 A1 | 9/2010 | Biedermann et al. | |
| 2010/0256686 A1 | 10/2010 | Fisher | |
| 2010/0262195 A1 | 10/2010 | Jackson | |
| 2010/0274288 A1 | 10/2010 | Prevost et al. | |
| 2010/0298891 A1 | 11/2010 | Jackson | |
| 2010/0305621 A1 | 12/2010 | Wang et al. | |
| 2011/0040338 A1 | 2/2011 | Jackson | |
| 2011/0077694 A1 | 3/2011 | Biedermann et al. | |
| 2011/0152949 A1 | 6/2011 | Biedermann et al. | |
| 2011/0160778 A1 | 6/2011 | Elsbury | |
| 2011/0196430 A1 | 8/2011 | Walsh et al. | |
| 2011/0213424 A1 | 9/2011 | Biedermann et al. | |
| 2011/0282399 A1 | 11/2011 | Jackson | |
| 2012/0010661 A1 | 1/2012 | Farris et al. | |

(56) References Cited

U.S. PATENT DOCUMENTS

| | | |
|---|---|---|
| 2012/0035670 A1 | 2/2012 | Jackson et al. |
| 2012/0046699 A1 | 2/2012 | Jones et al. |
| 2012/0046700 A1 | 2/2012 | Jackson et al. |
| 2012/0078307 A1 | 3/2012 | Nihalani |
| 2012/0150239 A1 | 6/2012 | Garamszegi |
| 2012/0179212 A1 | 7/2012 | Jackson et al. |
| 2012/0209336 A1 | 8/2012 | Jackson |
| 2012/0232598 A1 | 9/2012 | Hestad et al. |
| 2012/0303070 A1 | 11/2012 | Jackson |
| 2012/0310284 A1 | 12/2012 | Gerchow |
| 2012/0310290 A1 | 12/2012 | Jackson |
| 2013/0046345 A1 | 2/2013 | Jones et al. |
| 2013/0338721 A1 | 2/2013 | Biedermann et al. |
| 2013/0072981 A1 | 3/2013 | Jackson |
| 2013/0096620 A1 | 4/2013 | Biedermann et al. |
| 2013/0096621 A1 | 4/2013 | Biedermann et al. |
| 2013/0096622 A1 | 4/2013 | Biedermann et al. |
| 2013/0103098 A1 | 4/2013 | Jackson et al. |
| 2013/0144346 A1 | 6/2013 | Jackson et al. |
| 2013/0150852 A1 | 6/2013 | Shluzas et al. |
| 2013/0197586 A1 | 8/2013 | Matthis |
| 2013/0211465 A1 | 8/2013 | Savage |
| 2014/0025119 A1 | 1/2014 | Biedermann et al. |
| 2014/0058454 A1 | 2/2014 | Hammer |
| 2014/0081334 A1 | 3/2014 | Jackson |
| 2014/0094849 A1 | 4/2014 | Spratt et al. |
| 2014/0121703 A1 | 5/2014 | Jackson et al. |
| 2014/0142634 A1 | 5/2014 | Schlaepfer et al. |
| 2014/0163619 A1 | 6/2014 | Harvey |
| 2014/0214097 A1 | 7/2014 | Jackson |
| 2014/0236239 A1 | 8/2014 | Biedermann et al. |
| 2014/0277157 A1 | 9/2014 | Chandanson et al. |
| 2014/0343617 A1 | 11/2014 | Hannen |
| 2014/0358182 A1 | 12/2014 | Puekert |
| 2015/0025579 A1 | 1/2015 | Biedermnn et al. |
| 2015/0032162 A1 | 1/2015 | Biedermann et al. |
| 2015/0134006 A1 | 5/2015 | Ziolo |
| 2015/0142059 A1 | 5/2015 | Biedermann et al. |
| 2015/0173816 A1 | 6/2015 | Biedermann et al. |
| 2015/0230829 A1 | 8/2015 | Harris et al. |
| 2016/0038204 A1 | 2/2016 | Biedermann et al. |
| 2016/0045228 A1 | 2/2016 | Biedermann et al. |
| 2016/0051289 A1 | 2/2016 | Gleason et al. |
| 2016/0367293 A1 | 12/2016 | Keyer et al. |
| 2017/0119437 A1 | 5/2017 | Harper et al. |
| 2017/0128104 A1 | 5/2017 | Nichols et al. |
| 2017/0135729 A1 | 5/2017 | Garamszegi |
| 2017/0181776 A1 | 6/2017 | Beretta |
| 2017/0189074 A1 | 7/2017 | Biedermann et al. |
| 2017/0209185 A1 | 7/2017 | Trautwein et al. |
| 2017/0224386 A1 | 8/2017 | Leff et al. |
| 2017/0224387 A1 | 8/2017 | Matthis et al. |
| 2017/0245897 A1 | 8/2017 | Nichols et al. |
| 2017/0265902 A1 | 9/2017 | Jackson |
| 2017/0296235 A1 | 10/2017 | Chandanson et al. |
| 2017/0340360 A1 | 11/2017 | Schlaepfer et al. |
| 2017/0354443 A1 | 12/2017 | Jackson |
| 2018/0000523 A1 | 1/2018 | Jackson |
| 2018/0014859 A1 | 1/2018 | Biedermann et al. |
| 2018/0098795 A1 | 4/2018 | Jackson |
| 2018/0250036 A1 | 9/2018 | Jackson et al. |
| 2018/0325560 A1 | 11/2018 | Jackson et al. |
| 2018/0360499 A9 | 12/2018 | Jackson |
| 2019/0053829 A1 | 2/2019 | Biedermann et al. |
| 2019/0059953 A1 | 2/2019 | Keyer |
| 2019/0117271 A1 | 4/2019 | Jackson et al. |
| 2019/0142468 A1 | 5/2019 | Jackson et al. |

* cited by examiner

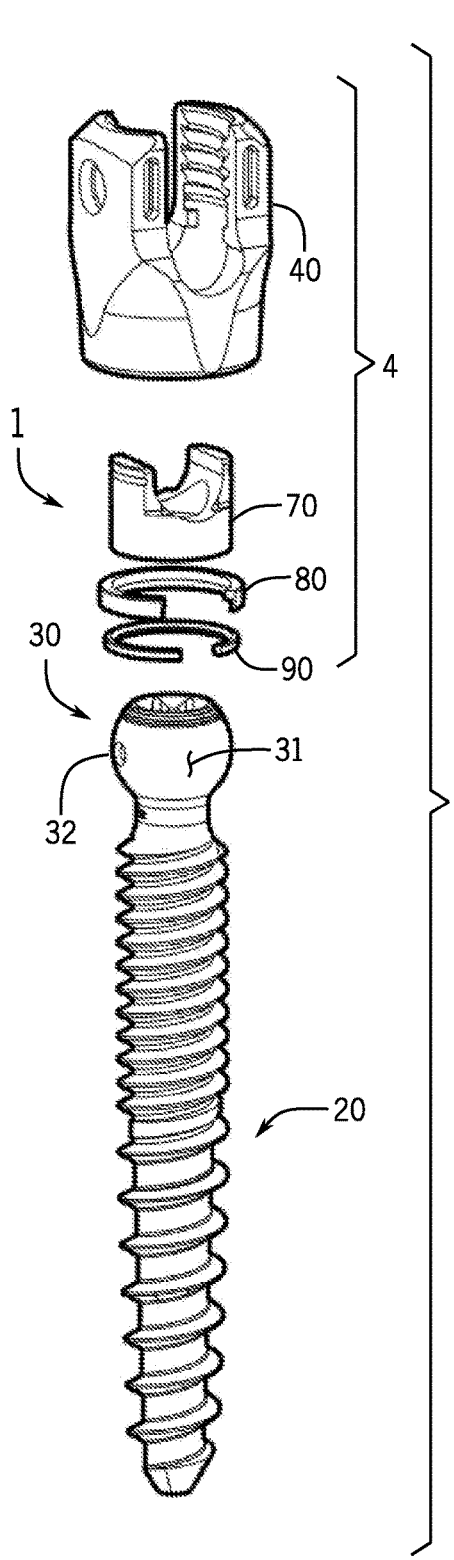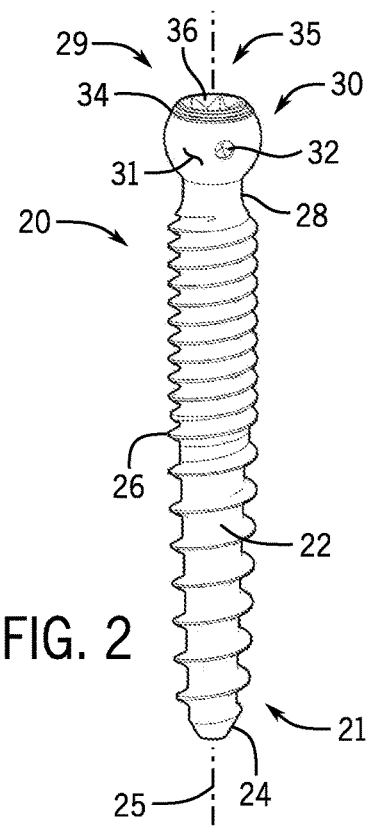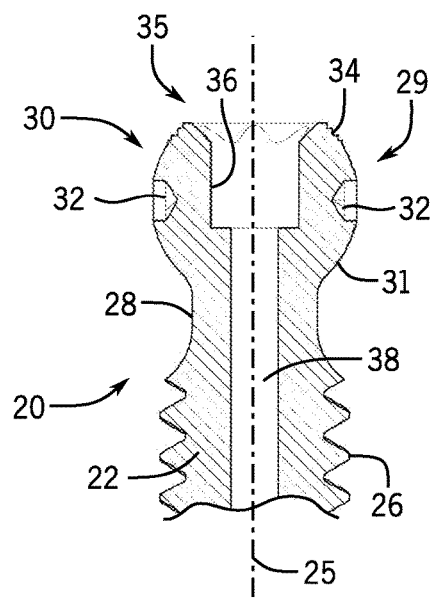
FIG. 1
FIG. 2
FIG. 3

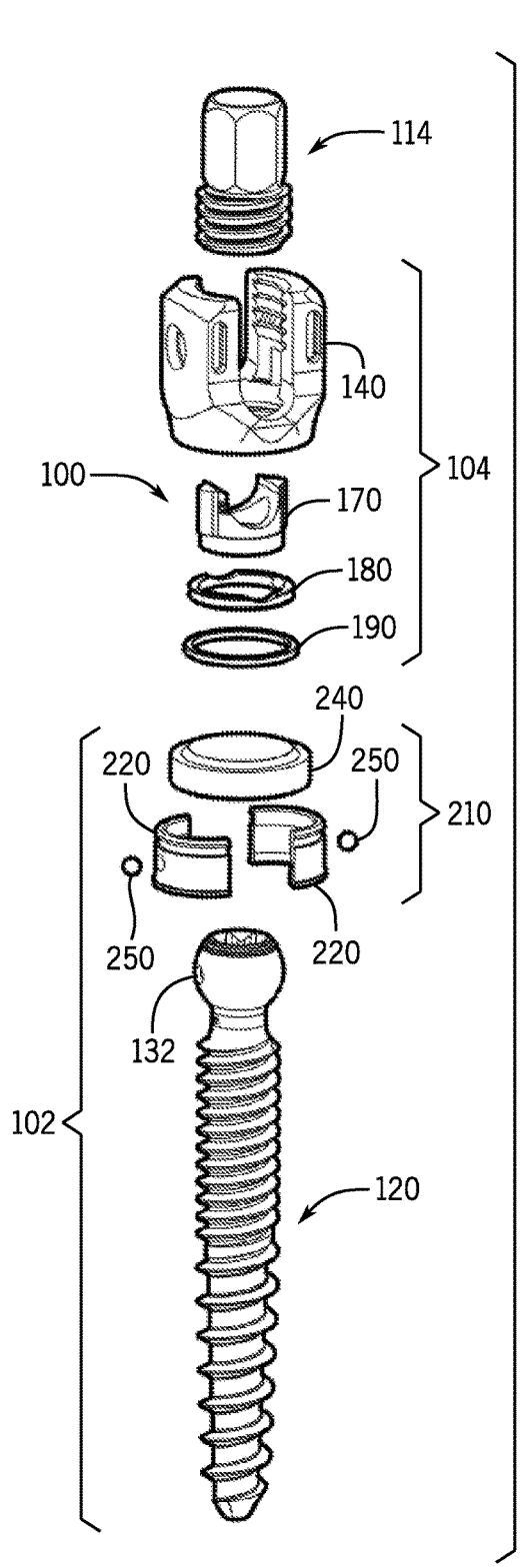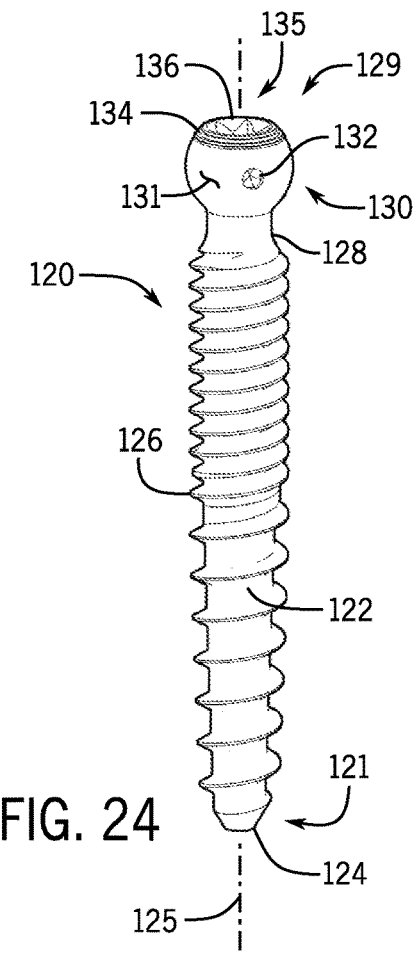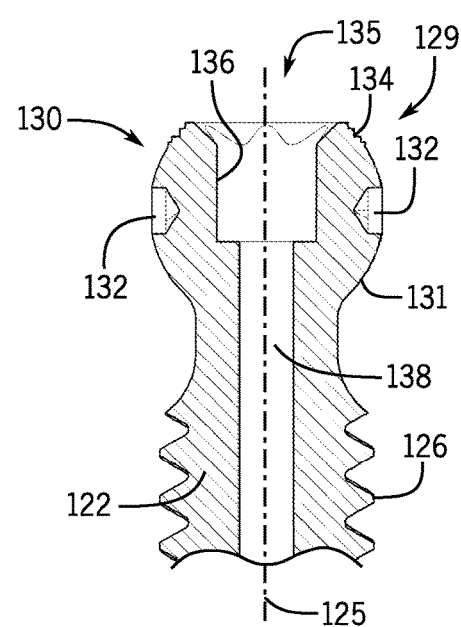
FIG. 23
FIG. 24
FIG. 25

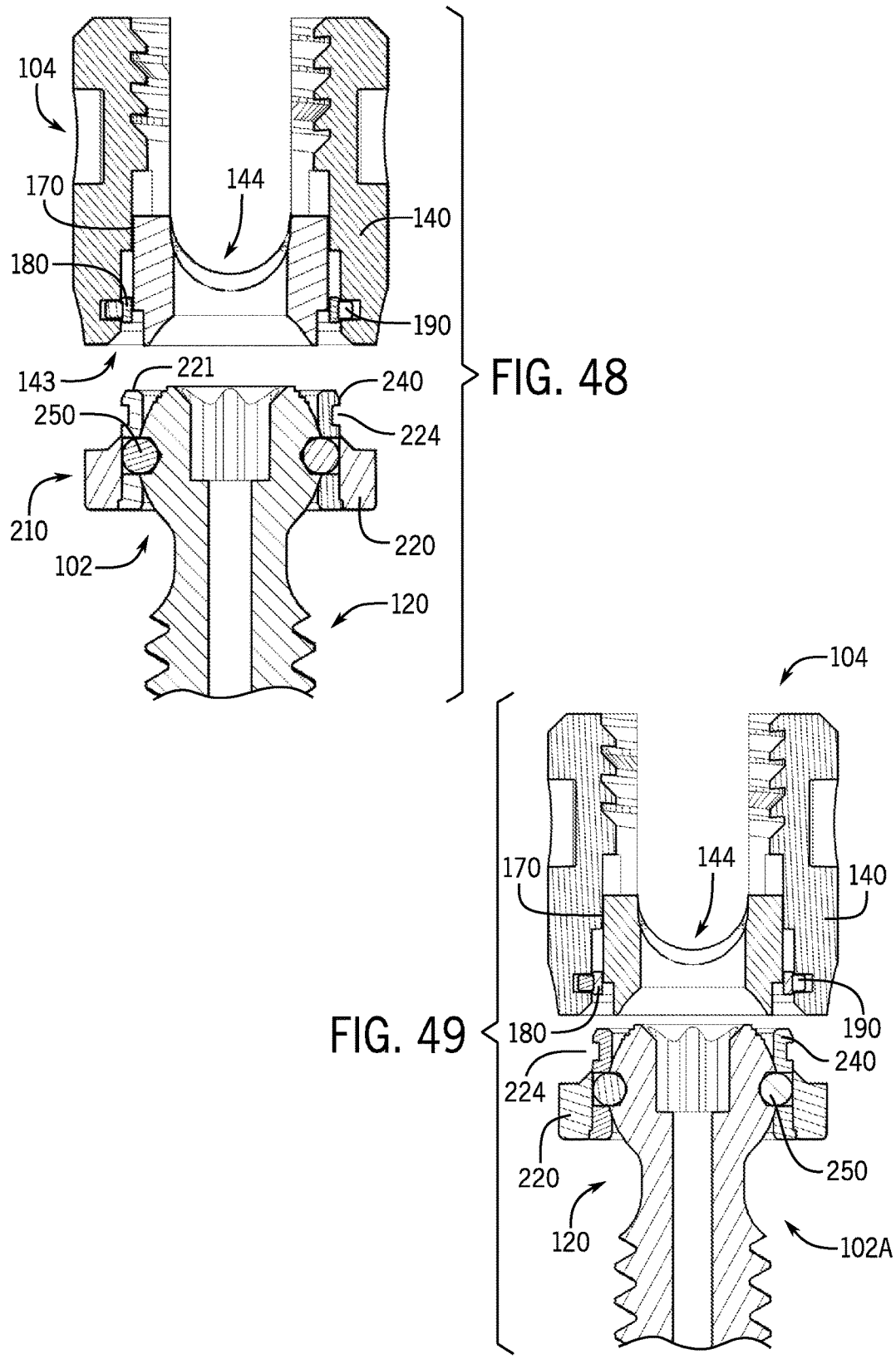

PIVOTAL BONE ANCHOR ASSEMBLY HAVING AN OPEN RING POSITIONER FOR A RETAINER

CROSS-REFERENCE TO RELATED APPLICATIONS

This application is a continuation of U.S. patent application Ser. No. 15/629,709, filed Jun. 21, 2017, which claims the benefit of U.S. Provisional Patent Application No. 62/352,876, filed Jun. 21, 2016, and U.S. Provisional Patent Application No. 62/362,830, filed Jul. 15, 2016, each of which is incorporated by reference in its entirety herein, and for all purposes.

U.S. patent application Ser. No. 15/629,709 is also a continuation-in-part of U.S. patent application Ser. No. 15/521,163, filed Apr. 21, 2017, which is a of 371 application of international application number PCT/US15/56706, filed Oct. 21, 2015, each of which is incorporated by reference in its entirety herein, and for all purposes.

PCT/US15/56706 claims the benefit of U.S. Provisional Patent Application No. 62/212,253 filed Aug. 31, 2015, U.S. Provisional Patent Application No. 62/200,501 filed Aug. 3, 2015, U.S. Provisional Patent Application No. 62/200,491 filed Aug. 3, 2015, and U.S. Provisional Patent Application No. 62/194,955 filed Jul. 21, 2015, each of which is incorporated by reference in its entirety herein, and for all purposes.

PCT/US2015/056706 also claims the benefit of U.S. Provisional Patent Application No. 62/137,707 filed Mar. 24, 2015, U.S. Provisional Patent Application No. 62/137,713 filed Mar. 24, 2015, U.S. Provisional Patent Application No. 62/078,173 filed Nov. 11, 2014, U.S. Provisional Patent Application No. 62/078,154 filed Nov. 11, 2014, U.S. Provisional Patent Application No. 62/066,813 filed Oct. 21, 2014, and U.S. Provisional Patent Application No. 62/066,806 filed Oct. 21, 2014, each of which is incorporated by reference in its entirety herein, and for all purposes.

TECHNICAL FIELD

The present disclosure relates to medical apparatus and methods. More specifically, the present disclosure relates to configurable bone anchors and associated methods of manufacture and use.

BACKGROUND

Spinal surgery may entail a variety of surgical procedures aimed at, for example, reconstructing a patient's spine following a catastrophic accident or correcting a degenerative condition of the patient's spine. One such system for repairing the spine is using a spinal fixation system including screws and/or other bone anchors that are affixed to structures on a posterior aspect of a vertebra. The screws, for example, may be polyaxial (i.e., multi-planar) or uniplanar (i.e., monoplanar) screws that include a shank having thread features pivotally coupled with a head. The shank is conventionally coupled with the head by extending a distal end of the shank through a top opening in the head such that a proximal enlarged end of the shank resides in a cavity of the head where the cavity has a lower opening that restricts the proximal end portion of the head from extending through the lower opening in the head (i.e., top-loading). The proximal end portion of the shank may then pivot within the cavity to provide movement through one or more planes (e.g., polyaxial, uniplanar).

One or more rods are conventionally affixed to the screw via a top-loading or side-loading arrangement. The rods may be affixed to multiple screws, which may be affixed to pedicles of multiple vertebral bodies. Together, the system of screws and rods may act to stabilize the instrumented vertebral column to aid in the correction or reconstruction of the patient's spine.

While the aforementioned systems are known in the art, there is a need for additional systems and tools to further advance surgical spinal procedures. Such systems and tools will be discussed herein and may include snap-on, bottom-loaded screws, and other bone anchors that provide advantages over techniques, systems, and other bone anchors known in the art.

SUMMARY

Briefly described, one embodiment of the present disclosure comprises a pivotal bone anchor assembly that includes a shank sub-assembly comprising a shank and a coupler, and a receiver sub-assembly comprising a receiver having a bore with an expansion chamber formed therein above a bottom opening, as well as a separate internal snap-fit assembly that is located within the receiver bore proximate the bottom opening. The snap-fit assembly generally comprises an insert, a retainer ring positioned within the receiver expansion chamber, and a positioner configured to hold the retainer ring in a centralized position within the expansion chamber. The shank sub-assembly is uploaded through the receiver bottom opening such that the positioner is pushed up into a coupler chamber located above the expansion chamber while the retainer rings engages a circumferential locking groove of the coupler to secure the shank sub-assembly with the receiver sub-assembly with a snap-fit connection.

BRIEF DESCRIPTION OF THE DRAWINGS

FIG. 1 is an exploded perspective view of a bone anchor assembly, in accordance with a representative embodiment of the present disclosure.

FIG. 2 is a perspective side view of the shank of FIG. 1.

FIG. 3 is a cross-sectional side view of the head of the shank of FIG. 1.

FIG. 23 is an exploded perspective view of a bone anchor assembly that can be selectively configured for multi-planar or mono-planar pivoting motion, in accordance with another representative embodiment of the present disclosure.

FIG. 24 is a perspective side view of the shank of FIG. 23.

FIG. 25 is a cross-sectional side view of the head end of the shank of FIG. 23.

FIG. 48 is a cross-sectional side view of the shank sub-assembly of FIG. 23 with ball bearings and a receiver assembly including a receiver, insert, positioner, and retainer.

FIG. 49 is a cross-sectional side view of the shank sub-assembly of FIG. 48 with ball bearings being proximally advanced towards the receiver sub-assembly that includes the receiver, the insert, the positioner, and the retainer.

Figure 4:
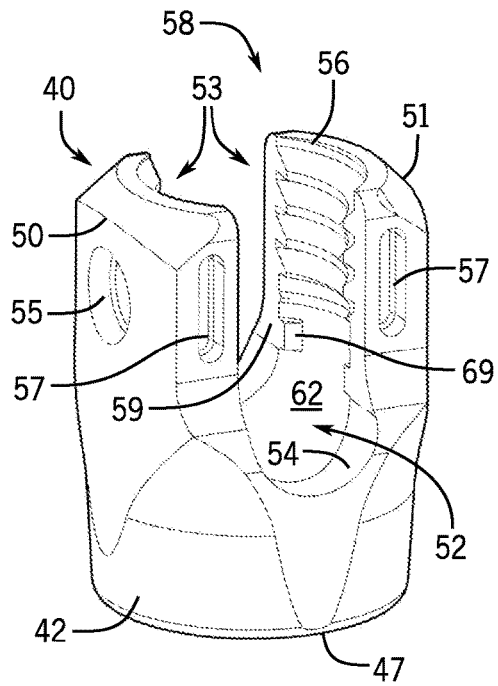
FIG. 4 is a perspective view of the receiver of FIG. 1.

Those skilled in the art will appreciate and understand that, according to common practice, various features and elements of the drawings described above are not necessarily drawn to scale, and that the dimensions of the various features and elements may be expanded or reduced to more clearly illustrate the embodiments of the present disclosure described therein.

DETAILED DESCRIPTION

The following description, in conjunction with the accompanying drawings described above, is provided as an enabling teaching of representative embodiments of a bone anchor having snap fit assembly between the shank and the receiver sub-assembly. It is to be understood, however, that the various embodiments described herein are merely exemplary of the bone anchor's disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

I. Multi-Planar Bone Screw Utilizing a Spherical Universal Shank

Referring now in more detail to the drawing figures, wherein like parts are identified with like reference numerals throughout the several views, FIGS. 1-22 illustrate a bone anchor apparatus or assembly 1 configured for multi-planar or polyaxial motion, in accordance with one representative embodiment of the present disclosure. While the bone anchor for the assembly 1 is generally a polyaxial bone screw, such as spherical universal shank 20, it is foreseen that the disclosure could be utilized with other types of spinal implants that utilize pressure inserts, such as polyaxial bone hooks or clamps, for example.

Figure 22:
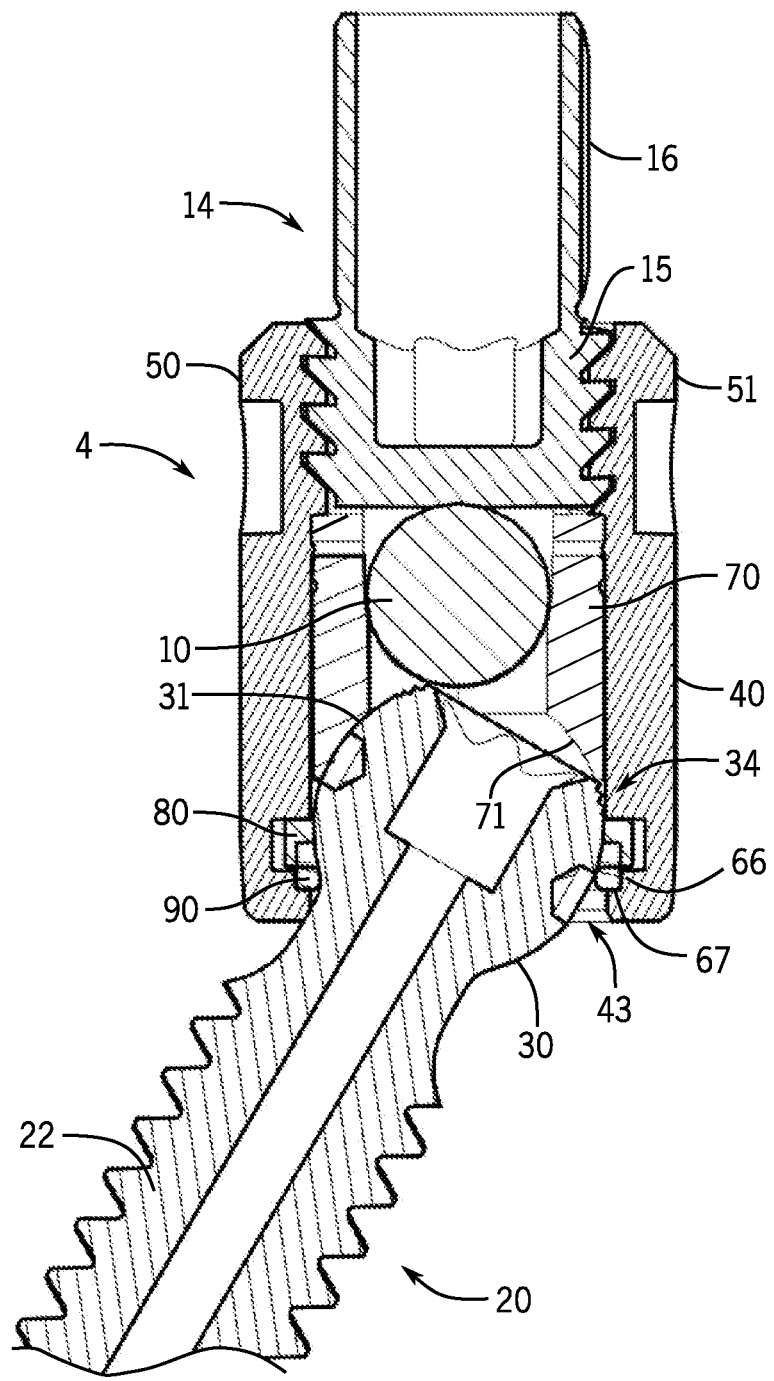
FIG. 22 is a cross-sectional side view of the receiver, insert, positioner, retainer, and shank, with a connecting rod and closure top securing the shank in a particular orientation relative to the receiver.

As shown in FIG. 1, the bone anchor assembly 1 generally includes a spherical universal shank 20 and a receiver sub-assembly 4 that further includes a receiver 40, a pressure insert 70, a positioner 80, and a retainer ring or retainer 90. The bone anchor assembly 1 can also include a closure 14 (FIG. 22). The bone anchor assembly 1 is generally adapted for use with an elongate rod or connecting member 10 (FIG. 22). In one aspect the receiver sub-assembly 4, including the receiver 40, the retainer ring 90, the positioner 80, and the insert 70, may be pre-assembled at a manufacturing facility prior to shipping, and then may be further assembled with the spherical universal shank 20 either prior or subsequent to implantation of the shank 20 into a vertebra (not shown), as will be described in greater detail below.

The receiver sub-assembly 4 and the spherical universal shank 20 cooperate in such a manner that the receiver sub-assembly 4 and the shank 20 can be secured at any of a plurality of angles, angulation, articulations, or angular alignments relative to one another and within a selected range of angles from side to side and from front to rear, to enable flexible or articulated engagement of the receiver sub-assembly with respect to the shank 20 until both are locked or fixed relative to each other near the end of an implantation procedure, as seen, for example, in FIG. 22, for optimal surgical relationship with the spinal column.

As shown greater detail in FIGS. 2-3, the spherical universal shank 20 can comprise an elongate body 22 having a distal end 21 and a proximal end 29 opposite the distal end. The elongate shank body 22 can further include a helically wound bone implantable thread 26 (single or multi start thread forms, which can have various types of thread patterns and cross sections) extending from near the neck 28 to the tip 24 of the body 22 and extending radially outwardly therefrom. During use, the body 22 can utilize the thread 26 for gripping and advancement as it is implanted into the vertebra (not shown) leading with the tip 24 and driven down into the vertebra with a suitable installation or driving tool (not shown), so as to be implanted into the vertebra to up near the neck 28. The shank 20 can also have a longitudinal centerline axis of rotation 25.

The proximal end 29 of the spherical universal shank 20 can further include a shank head 30 having a substantially spherically-shaped outer surface 31, with two opposed, co-linear bores 32 extending radially inward from the outer surface 31 toward the longitudinal axis 25 of the shank 20. The radial bores 32 can be closed bores of predetermined diameter and depth, and can have a conically-shaped end walls of pre-determined size and shape. As described in more detail below, the radial bores 32 are generally configured to receive a pair of spherical ball bearings that are operable, in combination with a coupler sub-assembly, to restrict or limit the motion of the spherical universal shank 20 relative to the receiver to mono-planar motion. Absent the ball bearings and the coupler sub-assembly, however, and per the embodiment of the bone anchor assembly 1 shown in FIG. 1, the spherical universal shank 20 is free to move relative to the receiver 40 with polyaxial or multi-planar motion until locked into an angular position by the final engagement of the rod 10 and closure 14 within the receiver sub-assembly 4, as shown in FIG. 22.

The shank head 30 can also include a tool engagement structure 36 or drive feature aligned with the longitudinal axis 25 of the shank 20 and extending downwardly or inwardly from the top end 35 of the spherical head 30. In one aspect the top end 35 of the spherical head 30 can further include a plurality of outwardly projecting insert engagement structures, such as concentric ridges 34. The insert engagement structures can be configured to engage or dig into a concave bottom surface of the pressure insert 70 (FIG. 1) so as to establish a more secure friction or interference fit between the proximal end 29 of the shank 20 and the insert 70 when the two components are ultimately locked together, as shown in FIG. 22.

Figure 5:
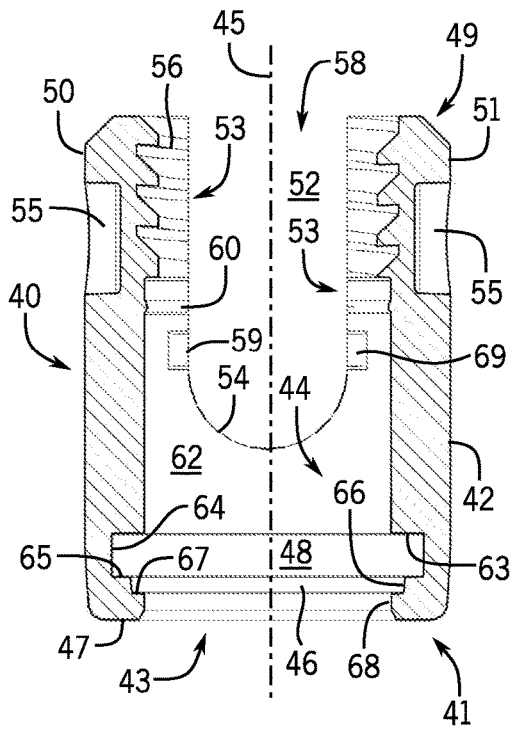
FIG. 5 is a cross-sectional side view of the receiver of FIG. 1.

The receiver component 40 of the receiver sub-assembly 4 is illustrated in detail in FIGS. 4-5, and generally includes a substantially cylindrical base 42 having a central cavity or bore 44 that is centered around a longitudinal axis 45 of the receiver 40. At the distal end 41 of the receiver 40 the bore 44 opens to the bottom surface 47 of the base 42 through bottom or distal opening 43. Integral with the base 42 is a pair of opposed upstanding arms 50 and 51 forming a cradle and defining a channel 52 between the arms 50 and 51 with an upper opening, generally 58, and a U-shaped lower seat 54, the channel 52 having a width for operably receiving the rod 10 between the arms 50, 51, as best seen in FIG. 22. Each of the arms 50 and 51 has an interior surface 53 that includes various inner cylindrical profiles and a discontinuous partial helically-wound guide and advancement structure 56 located adjacent top surfaces of each of the arms 50, 51. It is foreseen that the receiver may further include extensions (not shown) attached to the arms 50, 51 having break off junctures to the arms. The breakoff extensions can also have internal threads.

The discontinuous guide and advancement structure 56 can be a partial helically wound reverse angle thread form configured to mate under rotation with a similar fastener structure 15 formed into the closure 14 (FIG. 22). However, it is foreseen that the guide and advancement structure 56 could alternatively be a square-shaped thread, a buttress thread, an interlocking flange form or other thread-like or non-thread-like helically wound and non-helically wound discontinuous advancement structure for operably guiding, under complete or partial rotation, and advancing the closure 14 downward between the arms 50, 51, as well as eventual torqueing when a bottom of the closure 14 abuts against the rod 10. It is also foreseen that the closure 14 need not have a breakoff head 16 in certain embodiments.

With continued reference to FIGS. 4-5, an opposed pair of first tool receiving and engaging apertures or indentations 55 can be formed into outer side surfaces of the illustrated arms 50, 51. Furthermore, an additional two pairs of second tool receiving and engaging apertures 57 may be formed in front and rear surfaces of the arms 50, 51. Some or all of the apertures 55 and 57 may be used for holding the receiver 40 during the implantation of the shank body 22 (FIG. 2) into a vertebra when the shank is pre-assembled with the receiver 40, and during assembly of the bone anchor assembly 1 with the rod 10 and the closure structure 14. It is foreseen that the tool receiving grooves or apertures 55 and 57 may be configured in a variety of shapes and sizes and be disposed at other locations on the receiver arms 50, 51, such as near the top of the receiver arms in the form of horizontal radiused grooves.

Referring to FIG. 5 and returning to the interior surface 53 of the receiver arms 50, 51, moving downwardly, in a direction toward the base 42, adjacent the guide and advancement structure 56 is a discontinuous insert attachment structure, such as rounded ridge 60, that extends inwardly from the interior surface 53 of the receiver arms 50, 51. Adjacent to and located below the insert attachment ridge 60 is a cylindrically-shaped surface 62 that is oriented substantially parallel to the receiver longitudinal axis 45, and that is sized and shaped to receive the compression insert 70, as will be described in greater detail below. The cylindrical surface 62 extends downward from the insert attachment ridge 60 to surround the U-shaped lower seat 54 of the channel 52. Above the seat 54 the cylindrical surface 62 is by definition discontinuous, while below the seat 54 the cylindrical surface 62 can smoothly merge into a continuous cylindrical sidewall surface that defines the upper portion of the bore 44.

The cylindrical surface 62 can have an internal diameter that is sized to slidably receive the outer diameter of the insert 70 as it is inserted upwardly into the bore 44 and open channel 52 through the bottom opening 43 toward engagement with the insert attachment structure 60. Moreover, the interior surfaces 53 of the receiver arms 50, 51 can further include spaced-apart guide projections 59 projecting inward into the channel 52 below the insert attachment structure 60 and having opposing faces that define guide surfaces 69 which slidably engage with corresponding cut-out side surfaces 78 of the insert 70 to prevent the insert from rotating within the receiver 40 upon insertion into the bore 44.

An upper annular shelf or stop surface 63 is located below the cylindrical surface 62, and is disposed substantially perpendicular to the receiver longitudinal axis 45 to form an upper stop for the positioner 80, prohibiting the positioner 80 from moving upwardly into the upper portion of the bore 44 that receives the compression insert 70. In one aspect the upper stop surface 63 can further define the upper surface of an expansion chamber 48, with cylindrical surface 64 and lower annular shelf or stop surface 65 further defining the sidewall surface and lower surface of the expansion chamber 48, respectively. The lower annular stop surface 65 is also disposed substantially perpendicular to the receiver longitudinal axis 45, and has an inner boundary at a downwardly-extending intermediate cylindrical surface 66 having a diameter that is greater than the diameter of cylindrical surface 62 that defines the upper portion of the bore 44.

The intermediate cylindrical surface 66 extends downward to a lower annular step or seating surface 67. Lower annular step surface 67 in turn extends inward to another downwardly-extending distal cylindrical surface 68 having a diameter less than the diameter of the intermediate cylindrical surface 66, and that defines the distal or bottom opening 43 of the receiver 40. As described in more detail below, the intermediate cylindrical surface 66 and lower annular step surface 67 can together define, in stepwise fashion, a locking chamber 46 that ultimately receives and secures the non-pivoting retainer 90 to the receiver 40 upon completion of the bone anchor assembly, wherein the non-pivoting retainer 90 seated on the annular step surface 67 can expand slightly outward to frictionally engage the cylindrical surface 66, when in a locked position, as is shown, for example, in FIG. 22.

As described above, the upper stop surface 63, the sidewall cylindrical surface 64, and the lower stop surface 65 partially define a circumferential recess or expansion chamber 48 that is sized and shaped to house the positioner 80 and to receive the non-pivoting retainer 90 as it expands around the spherical head 30 of the shank as the head 30 moves upwardly through the bore 44 during assembly. Additionally, the expansion chamber 48 forms a restriction to prevent the positioner 80 from moving upwardly with the shank head 30, with the annular upper stop surface 63 preventing the positioner 80, and ultimately the non-pivoting retainer 60 from passing from the expansion chamber 48 into the upper portion of the bore 44, whether the non-pivoting retainer 90 is in an expanded state or in a nominal or neutral state (i.e., without compression or tension).

Distal cylindrical surface 68 can be joined or connected to an exterior bottom surface 47 of the base 42 by one or more beveled, curved or conical surfaces, and defines the bottom opening 43 of the receiver 40. The lower opening 43 is circularly shaped having a diameter or width or radius (not shown) measured from one side of the distal cylindrical surface 68 to the next. In one aspect the distal cylindrical surface 68 can have a diameter that is substantially the same as the diameter of the cylindrical surface 62 of the upper bore 44, allowing for slidable uploading of the compression insert 70 while requiring compression or squeezing of both the non-pivoting retainer 90 and the positioner 80 during their uploading into the receiver 40 through the lower opening 43.

Figure 6:
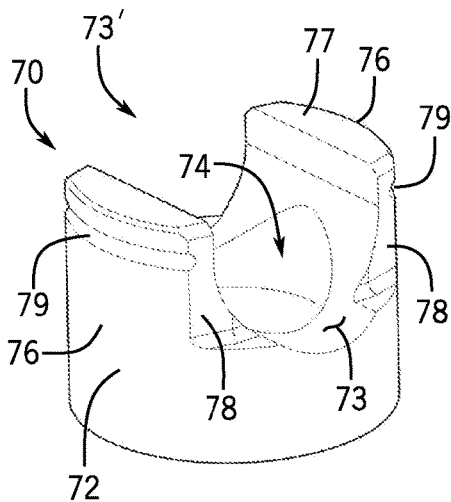
FIG. 6 is a perspective view of the insert of FIG. 1.
Figure 7:
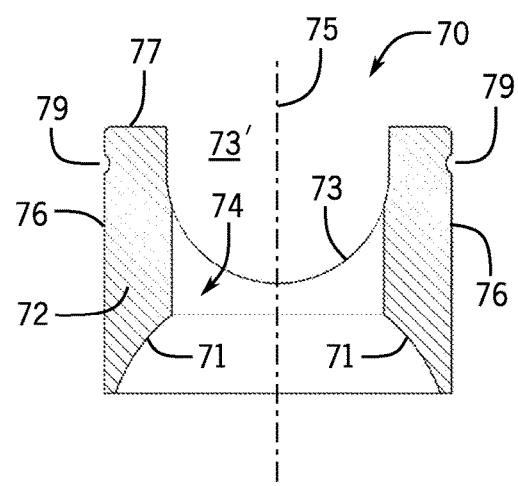
FIG. 7 is a cross-sectional side view of the insert of FIG. 1.

With reference to FIGS. 1 and 6-7, the friction fit compression or pressure insert 70 is sized and shaped to be loaded into the bore 44 of the receiver 40, for example, through the bottom opening 43. The illustrated insert 70 has a central axis 75 operationally aligned with the central axis 45 of the receiver 40. In operation, a concave shank head engagement surface 71 formed into the bottom face of the insert 70 advantageously frictionally engages with the outer surface 31 of the bone screw shank head 30, allowing for un-locked, but non-floppy placement of the angle of the shank 20 with respect to the receiver 40 during surgery, prior to locking of the shank 20 with respect to the receiver 40 near the end of the procedure with a rod or connecting member 10 and a closure 14, as shown in FIG. 22. It is foreseen that the insert 70 may be made from a resilient material, such as a stainless steel or titanium alloy, or a polymer, or some combination thereof, so that portions of the insert may be expanded about and then contracted, snapped or popped onto the shank head 30 as well as over the insert attachment ridge 60. Furthermore, in operation, the insert 70 is suspended within the receiver 40, being frictionally held in place by the insert attachment ridge 60 projecting inward from the inner surfaces 53 of the receiver upright arms 50, 51. In this way the insert 70 is be prohibited from moving upward or downward until deployed, even during the initial insertion of the shank head 30 into the receiver 40. As will be explained in greater detail below, after initial assembly and during operation of the bone anchor assembly 1, preferably neither the non-pivoting retainer 90 nor the inner cylindrical surface 62 of the receiver 40 that defines the cavity or bore 44 place any compressive force on the insert 70 to hold the shank head 30 therein.

The illustrated insert 70 generally includes a substantially cylindrically shaped lower body 72 with a pair of spaced apart upstanding arms 76 having top surfaces 77. The upstanding arms 76 can have a cylindrically-shaped outer surface on each side which are substantially smooth and vertically or axially opposed, but radially spaced from the center axis 75. The outer surface of each arm 76 can further include a circumferentially-extending rounded receiver attachment recess 79 spaced a predetermined distance from the top surfaces 77 thereof. Each receiver attachment recess 79 can extend discontinuously circumferentially about the outer surface of the arm 76, and can have a width and radius of curvature that is substantially similar to the width and radius of curvature of the complimentary insert attachment ridge 60 projecting inward from the inner surfaces 53 of the receiver upright arms 50, 51 (FIGS. 4-5).

The inner surfaces of the insert upstanding arms 76 can include proximal-facing saddle or seating surfaces 73 that form a U-shaped insert channel 73' therebetween for receiving and engaging the underside surface of the elongate rod. There is also an axially aligned and centered through bore 74 that runs from the top to the bottom of the insert 70. The bore 74 is defined by an inner cylindrical surface that is at least partially bounded on the upper end by the U-shaped channel seating surfaces 73 and on the lower end by the concave shank head engagement surface 71. The through bore 74 is sized and shaped to receive a driving tool (not shown) there through that can engage with the shank tool engagement structure 36 when the shank body is driven into bone with the receiver attached or without. It is foreseen that the insert shank head engagement surface 71 may comprise a roughened or textured surface or surface finish, or may be scored, grit blasted, knurled, or the like, for enhancing frictional engagement with the shank head 30.

In addition, the sides of the insert upstanding arms 76 can further include cut-out sections with flat side surfaces 78 that are size and shaped to be received between the spaced-apart guide projections 59 projecting inward into the receiver channel 52 below the insert attachment structure 60. The insert flat side surfaces 78 can slidably engage with the opposing receiver guide surfaces 69 in a manner that allows for upward and downward translation of the insert 70 within the receiver bore 44 while preventing rotation of the insert around the receiver longitudinal centerline axis 45. This ensures that the insert channel 73' is aligned with the receiver channel 52, and with the elongate rod 10 being received by the insert saddle or seating surfaces 73 and spaced from the interior surfaces 53 of the receiver arms 50, 51 by the thickness of the insert upstanding arms 76, as shown in FIG. 22.

Figure 8:
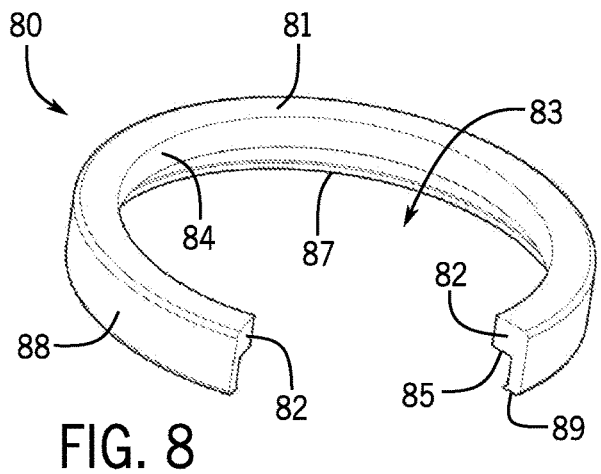
FIG. 8 is a perspective view of the positioner of FIG. 1.
Figure 9:
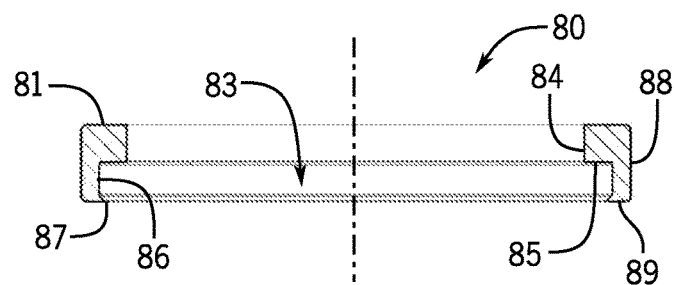
FIG. 9 is a cross-sectional side view of the positioner of FIG. 1.

With reference to FIGS. 1 and 8-9, the positioner 80 can generally comprise an open ring-shaped body made from a resilient material, such as a stainless steel, titanium alloy, cobalt chrome, or the like, as well as polymers, or some combination thereof, so that the positioner 80 may be expanded and contracted during various steps of assembly, as will be described in greater detail below. The positioner 80 can also have a central axis that is operationally aligned with both the receiver axis 45 and the central axis of the non-pivoting retainer 90, and that may also be aligned with shank axis 25.

The ring-shaped positioner 80 has a central aperture, generally 83, that passes entirely through the positioner body from a top surface 81 to a bottom surface 89 thereof. The surfaces that define the aperture 83 include a discontinuous upper inner cylindrical surface 84 adjacent the top surface 81, a discontinuous shelf or abutment surface 85 adjacent the upper inner cylindrical surface 84, and a discontinuous lower inner cylindrical surface 86, with each surface being coaxial with the positioner axis 85 when the positioner 80 is in a neutral non-compressed, non-expanded orientation or state. The upper inner cylindrical surface 84 can have a curvature similar to that of the outer surface 31 of the spherical shank head 30, so as to mate better with the curved surface of the shank head 30. The positioner 80 further includes an outer cylindrical surface 88 that is also oriented parallel to the positioner central axis. In one aspect the positioner 80 can further include a lower lip 87 projecting inward from the bottom of the lower inner cylindrical surface 86 adjacent the bottom surface 89. The lower lip 87 can be useful for better capturing or securing the retaining ring within the positioner in the as-shipped configuration, as described in more detail below.

Figure 15:
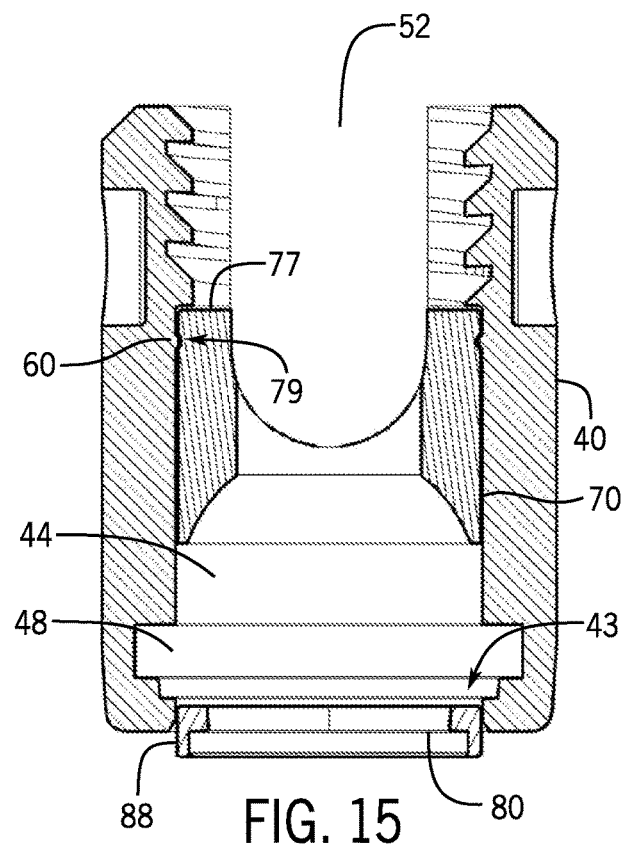
FIG. 15 is a cross-sectional side view of the receiver with the insert positioned in its second axial position, where the positioner is being uploaded through the bottom opening of the receiver.
Figure 16:
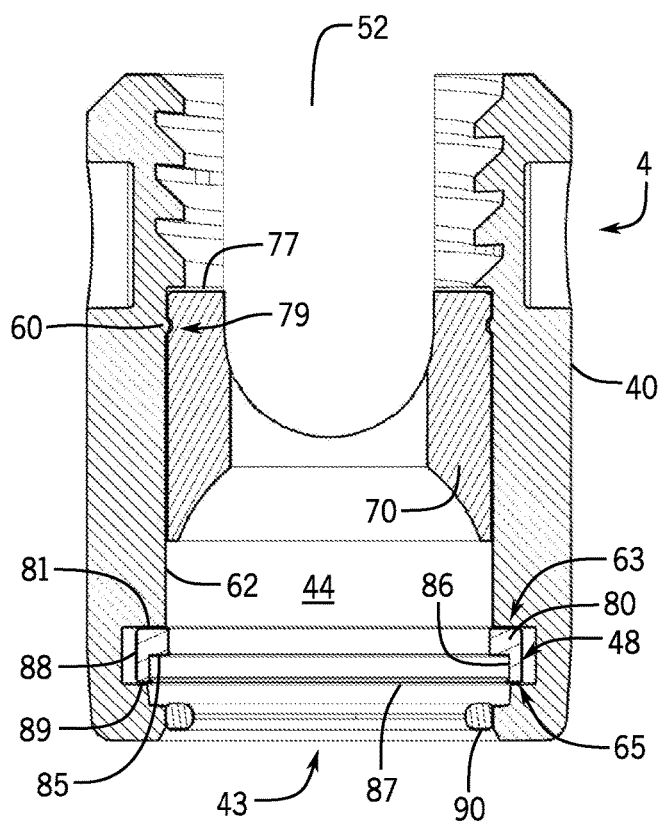
FIG. 16 is a cross-sectional side view of the receiver, insert, and positioner, where the retainer is proximally advanced through the bottom opening of the receiver and into the expansion chamber of the receiver.

The resilient positioner 80 further includes first and second end surfaces 82 disposed in spaced relation to one another when the retainer is in a neutral non-compressed state. Both end surfaces 82 can be disposed substantially perpendicular to the top surface 81 and the bottom surface 89. A gap having nominal width between the end surfaces 82 is determined by a desired amount of compressibility of the open positioner 80 when loaded into the receiver 40. The space shown in FIG. 8 provides adequate space between the end surfaces 82 for the positioner 80 to be pinched, with the end surfaces 82 compressed toward one another to a closely spaced or even touching configuration, if necessary, to an extent that the compressed positioner 80 is up or bottom loadable through the receiver bottom opening 43, as shown in FIG. 15. After passing through the receiver bottom opening 43 and upward to the upper annular shelf or stop surface 63, the positioner 80 can be allowed to expand or spring back to an original uncompressed, rounded or collar-like configuration, as shown in FIG. 16. The embodiment of the resilient positioner 80 shown in FIG. 8 illustrates the end surfaces 82 as being substantially parallel; however, it is foreseen that it may be desirable to orient the end surfaces obliquely or at a slight angle depending upon the amount of compression desired during loading of the positioner 80 into the receiver 40.

Figure 10:
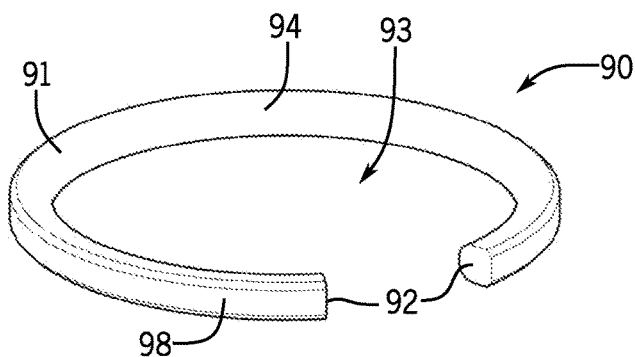
FIG. 10 is a perspective view of the retainer of FIG. 1.
Figure 11:
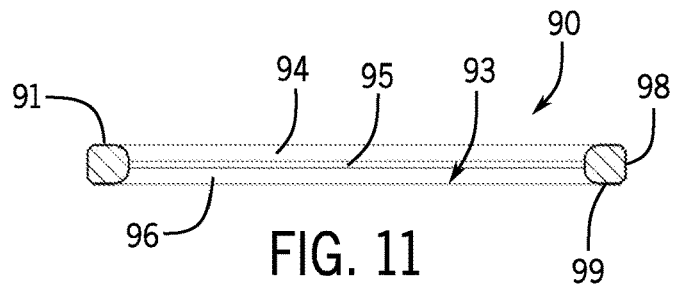
FIG. 11 is a cross-sectional side view of the retainer of FIG. 1.

With reference to FIGS. 1 and 10-11, the non-pivoting retainer 90 can generally comprise an open ring-shaped body made from a resilient material, such as a stainless steel or titanium alloy, cobalt chrome, or the like, or a polymer, or some combination thereof, so that the non-pivoting retainer 90 may be expanded during various steps of assembly, as will be described in greater detail below. It is foreseen that the retainer 90 may be made of a softer metal compared to that of the positioner 80, so that the positioner 80 is able to overpower or be structurally stronger than the non-pivoting retainer 90 in assembly.

Similar to the positioner 80, the non-pivoting retainer 90 has a central aperture 93 that passes entirely through the retainer 90 from a top surface 91 to a bottom surface 99 thereof. The non-pivoting retainer 90 is configured to not pivot with the shank 20 (FIGS. 2-3), but is situated to ultimately stay within the confines of the receiver locking chamber 46 (FIG. 5). Surfaces that define the central aperture 93 include a discontinuous upper inner curvate surface 94 adjacent the top surface 91 and a discontinuous lower inner curvate surface 96 adjacent the bottom surface 99. In one aspect a narrow substantially-planar midline surface 95 can separate the upper inner curvate surface 94 and the lower inner curvate surface 96 at the midline between the top surface 91 and the bottom surface 99, as shown in FIGS. 10-11. In other aspects, however, the upper and lower inner curvate surfaces can seamlessly merge together to form one continuous inner curvate surface that defines the central aperture 93.

The non-pivoting retainer 90 further includes an outer cylindrical surface 98 extending between the top surface 91 and the bottom surface 99. The outer surface 98 is oriented parallel to the retainer axis 95, and it is foreseen that the outer corners located about either the top surface 91 or bottom surface 99 could be rounded or beveled as needed. It is also foreseen that two or more evenly spaced notches or bumps (not shown) may be formed in the top surface 91, outer surface 98, or bottom surface 99 to more evenly distribute stress across the entire non-pivoting retainer 90 during contraction and expansion thereof.

The resilient non-pivoting retainer 90 further includes first and second end surfaces 92 disposed in opposed spaced relation to one another when the retainer 90 is in a neutral non-compressed state. Both end surfaces 92 can be disposed substantially perpendicular to the top surface 91 and the bottom surface 99 and parallel with retainer axis 95. The embodiment shown in FIG. 10 shows the slit or gap between the end surfaces 92 as being substantially parallel; however, it is foreseen that it may be desirable to orient the end surfaces obliquely or at a slight angle, depending upon the amount of compression desired during loading of the non-pivoting retainer 90 into the receiver 40.

A gap of nominal width between the end surfaces 92 can be determined by a desired amount of compressibility of the open non-pivoting retainer ring 90 when loaded into the receiver 40. The gap generally provides adequate space between the end surfaces 92 for the non-pivoting retainer 90 to be pinched, with the end surfaces being compressed toward one another to a closely spaced or even touching configuration, if necessary, to an extent that the compressed non-pivoting retainer 90 is up loadable through the receiver opening 43, as seen in FIG. 16. After passing upward through the retainer bottom opening 43 and through the lower portion of the bore 44 toward the previously installed positioner 80, the non-pivoting retainer 90 can be allowed to expand or spring back to its nominal and uncompressed collar-like shape. In one aspect the end portions of the retainer 90 adjacent the end surfaces 92 can be overlappingly compressed together in order to reduce the diameter of the retainer 90 to the point that the retainer will fit through the bottom opening 43 in the receiver 40.

It is also foreseen that the top surface 91 and portions of the outer surface 98 of the retainer 90 may additionally or alternatively include a roughened or textured surface or surface finish, or may be scored, knurled, grit blasted, or the like, for enhancing frictional engagement with the intermediate cylindrical inner surface 66 of the receiver locking chamber 46, as well as the interior of the positioner 80. The additional surface treatment may be useful for preventing or limiting rotational movement of the retainer 90 with respect to the positioner 80 and/or retainer 40 after assembly and before reaching the final locked configuration.

FIGS. 12-17 illustrate the sequential assembly of all the separate components of the receiver sub-assembly 4 into an 'as-shipped' configuration, at which the receiver sub-assembly 4 is configured for a simple 'snap-fit' assembly step onto the head 30 of the universal spherical shank 20. In one aspect the pre-assembly of the receiver sub-assembly 4 can take place in a controlled factory or manufacturing setting. FIGS. 18-21 then illustrate the assembly or coupling of the pre-assembled receiver sub-assembly 4 with the universal spherical shank 20, such as would take place within or near to an operating room setting by a medical professional, such as by a surgical technician or by the surgeon herself. An illustration of one exemplary final configuration of the assembled bone screw assembly 1 that includes the elongate rod 10 secured within receiver channel 52 by the closure 14, is then provided in FIG. 22.

Figure 12:
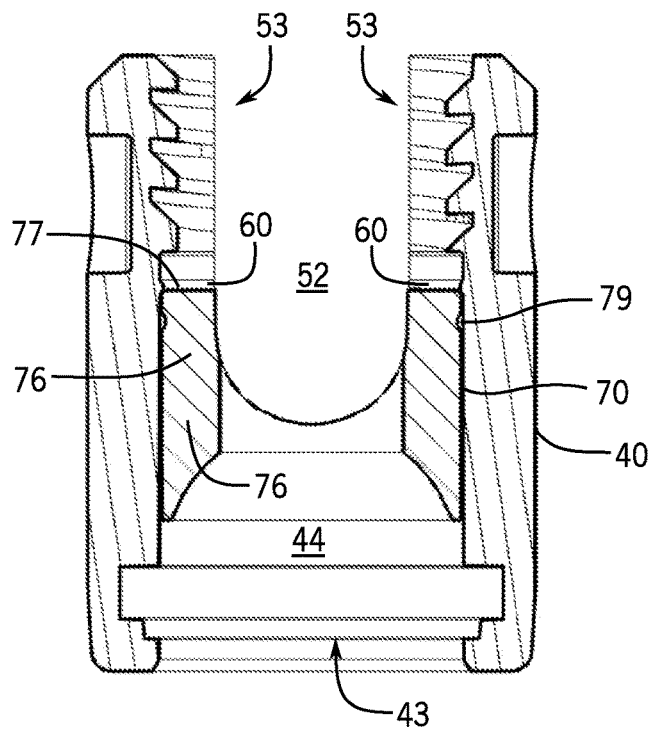
FIG. 12 is a cross-sectional side view of the receiver with the insert positioned therein.

The insert 70, positioner 80, and retainer ring 90 can be bottom-loaded through the distal opening 43 of the receiver 40 during pre-assembly of the receiver sub-assembly 4. For example, as shown in FIG. 12, the insert 70 is first inserted through the distal opening 43 and proximally advanced through the bore 44 and into the channel 52 of the receiver 40, until the top surfaces 77 of the insert upstanding arms 76 abut against the rounded bottom portion of the inwardly-projecting discontinuous insert attachment ridge 60. At this point the insert 70 is in a first axial position with further proximal advancement of the insert 70 within the receiver 40 being restricted by the insert attachment ridge 60.

Figure 13:
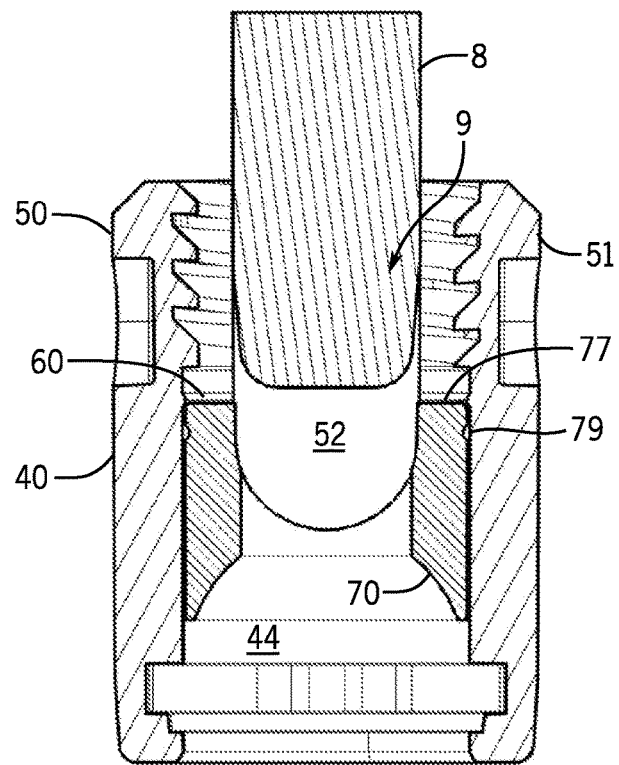
FIG. 13 is a cross-sectional side view of the receiver with the insert and a distal end of a splay tool positioned therein.
Figure 14:
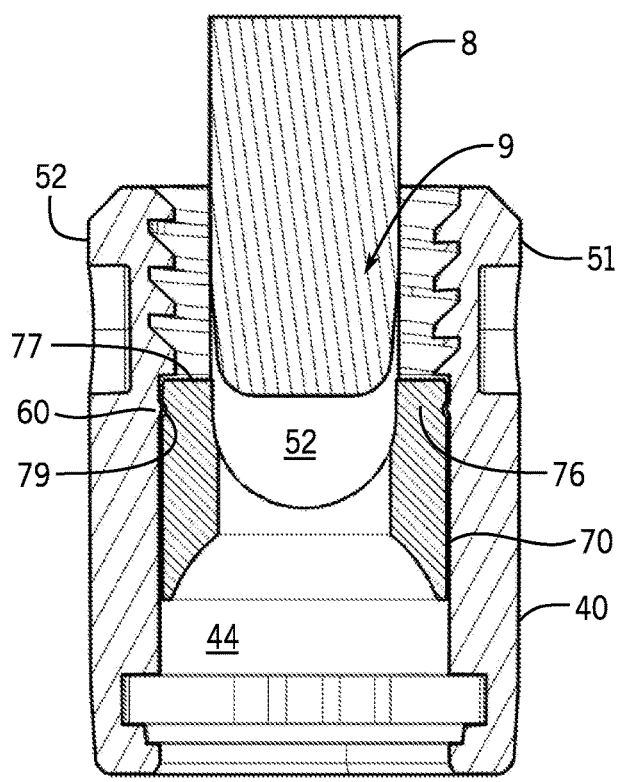
FIG. 14 is a cross-sectional side view of the receiver with the insert and a distal end of the splay tool positioned therein, where the insert is proximally displaced.

Next, as seen in FIG. 13, a distal end 9 of a splay tool 8 can be advanced distally into the U-shaped channel 52 of the receiver 40 to separate, splay, or slightly outwardly flex the opposing upright arms 50, 51 of the receiver 40 and temporarily expand the receiver channel 52. Once the opposing upright arms 50, 51 of the receiver 40 have been splayed apart a sufficient amount, the insert 70 may then be further proximally advanced to a second, upper-most axial position in which the circumferential receiver attachment recesses 79 formed into the outer surface of the insert upstanding arms 76 are axially aligned with and cover the corresponding insert attachment ridge 60 projecting from the inner surface 53 of the receiver arms 50, 51, as shown in FIG. 14. Once the insert 70 reaches the second axial position, the splay tool 8 may be removed so that the opposing upright arms 50, 51 of the receiver 40 can return to their earlier non-flexed positions and the insert attachment ridge 60 is captured within the circumferential receiver attachment recesses 79 of the insert arms 76 (FIGS. 6-7), so that downward pressure applied either by tooling or by the elongate rod member is now required to downwardly displace or deploy the insert 70 from its second axial position back to the first axial position. In this way the insert 70 can be firmly secured and maintained in its upper-most second axial position within the receiver 40 throughout shipping and even through the first snap-fit step of coupling the receiver sub-assembly 4 to the shank 20 with only the positioner 80 and retainer 90, as described below.

With the insert 70 secured in its second axial position, as shown in FIG. 15, the positioner 80 can be compressed or pinched (e.g. with an external force), as described above, so that its end surfaces 82 approach each other and its diameter is reduced sufficiently for the positioner 80 to be uploaded through the receiver distal or bottom opening 43 and proximally advanced into the expansion chamber 48. As shown in FIG. 16, the compression force can then be released and the positioner 80 allowed to expand back to its neutral or nominal size within the expansion chamber 48. In one aspect the diameter of the positioner's outer cylindrical surface 88 can be greater than the diameter of the receiver's inner cylindrical surface 62 that defines the upper bore 44, so that the top surface 81 of the positioner 80 in its nominal and uncompressed state will abut the upper annular shelf or stop surface 63 that defines the upper surface of the expansion chamber 48 and be prevented from moving further upward into the upper portion of the receiver bore 44.

Figure 17:
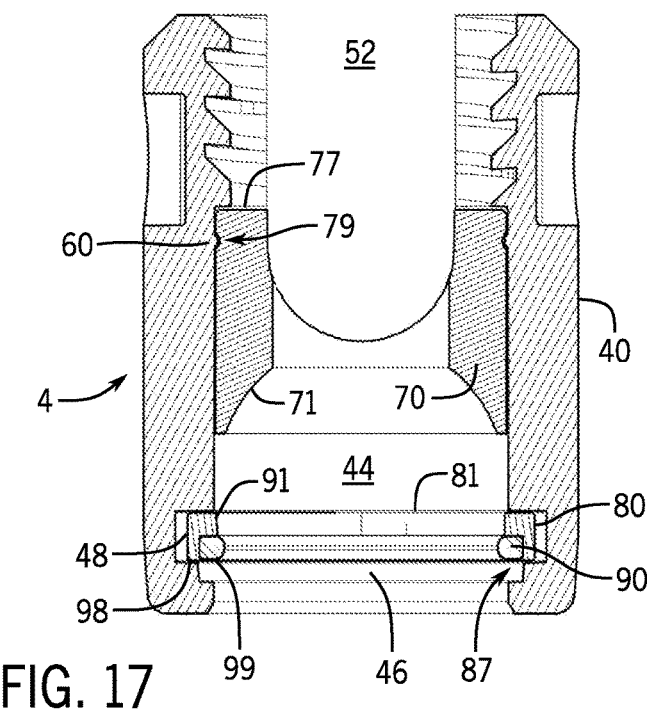
FIG. 17 is a cross-sectional side view of the receiver, insert, and positioner, where the retainer is proximally advanced through the bottom opening of the receiver and into engagement with the positioner.

With the positioner 80 now located within the expansion chamber 48, as shown in FIG. 16, the retainer 90 can be compressed or pinched (e.g. with an external force) as described above, so that its end surfaces 92 approach or overlap each other and its diameter is reduced sufficiently for the retainer 90 to be uploaded through the receiver distal or bottom opening 43 and proximally advanced into the expansion chamber 48 to contact the overlying discontinuous shelf surface 85 of the positioner 80. As shown in FIG. 17, the compression force can then be released and the retainer 90 allowed to expand back toward its neutral or nominal size so as to be firmly captured by the internal surfaces of the positioner 80, including the overlying shelf surface 85, the lower inner cylindrical surface 86, and the lower lip 87 projecting inward from the bottom of the lower inner cylindrical surface 86.

The non-pivoting retainer 90 can be adjusted such that the retainer top surface 91 abuts against the overlying positioner shelf surface 85 while the retainer outer surface 98 mates against the positioner lower inner cylindrical surface 86 with a friction fit, and with the positioner 80 being designed to compress slightly the non-pivoting retainer 90 within the interior confines or surfaces of the aperture 83, and thereby secure the retainer 90 into position within the positioner 80. In this combination, the gap between the positioner end faces 82 can be held a little wider while the positioner 80 applies a compressive force to the retainer 90, so that the gap between the retainer end faces 92 is at least partially closed. Thus, in one aspect the structural interaction of the positioner 80 and the non-pivoting retainer ring 90 can maintain the two components in a substantially concentric relationship and in a dynamic pre-loaded state. Moreover, the retainer 90 and the positioner 80 can also be situated or aligned together such that the gaps between their respective end faces 92, 82 are situated parallel with each other. It will also be appreciated, however, that this configuration with aligned gaps is not required in order for the combination to function as intended.

Although the positioner 80 and retainer 90 are uploaded separately into the retainer 40 in the illustrated embodiment, it will nevertheless be understood that the positioner 80 and the retainer 90 in combination may also be uploaded together into the receiver 40, as opposed to loading them separately as shown.

FIG. 17 further illustrates a preferred 'as-shipped' configuration or shipping state of the completed receiver sub-assembly 4, in which the retainer 90 is received within the positioner 80 while the positioner 80, in turn, is received within the expansion chamber 48 formed into the lower portion of the bore 44 of the receiver 40. The insert 70 is also received and secured within the channel 52 and the upper portion of the receiver bore 44 in its uppermost second axial position. Moreover, the bottom of the insert can also be sufficiently spaced above the top surface 81 of the positioner 80 so as to provide adequate clearance for the later step of pushing the shank head 30 upward through the apertures 93, 83 of the non-pivoting retainer 90 and positioner 80, respectively, without the shank head 30 becoming prematurely engaged with or restricted by the concave shank head engagement surface 71 of the insert 70. The pre-assembled receiver sub-assembly 4 is now ready for shipment as well as for assembly with the shank 20 either at the factory, at the spine company, by surgery staff prior to implantation, or directly after implanting the shank 20 by the surgeon.

Figure 18:
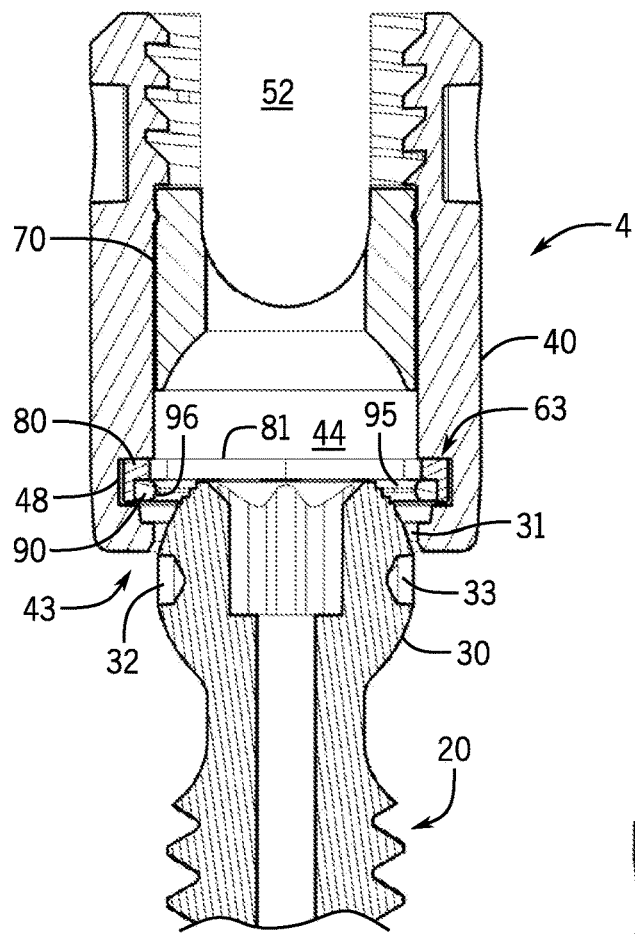
FIG. 18 is a cross-sectional side view of the receiver, insert, positioner, and retainer of FIG. 17, with the shank being proximally advanced relative to the receiver.

As illustrated in FIG. 18, the as-shipped receiver sub-assembly 4 may be coupled or snap-fit with the shank 20 by proximally advancing the head 30 of spherical universal shank 20 (with empty radial bores 32) through the distal opening 43 of the receiver 40 until the upper surface 31 of the spherical head abuts against the non-pivoting retainer 90, held down by the positioner 80. The non-pivoting retainer 90 and positioner 80 in combination are lifted up by the shank 20. The proximal driving of the shank 20 causes the top surface 81 of the positioner 80 to abut against the upper annular shelf or stop surface 63 (FIG. 5) of the interior bore 44 of the receiver 40, thereby arresting proximal displacement of the positioner 80 and non-pivoting retainer 90 combination within the confines of the expansion chamber 48 of the receiver 40. Also, the proximal (upward, as seen in FIG. 19) driving of the shank 20 causes the upper spherical surface 31 of the shank head 30 to abut against the discontinuous lower inner curvate surface 96 of the retainer 90, thereby causing the retainer 90 and the positioner 80 to radially expand as the shank head 30 proximally displaces into the confines of the bore 44 of the receiver 40.

Figure 19:
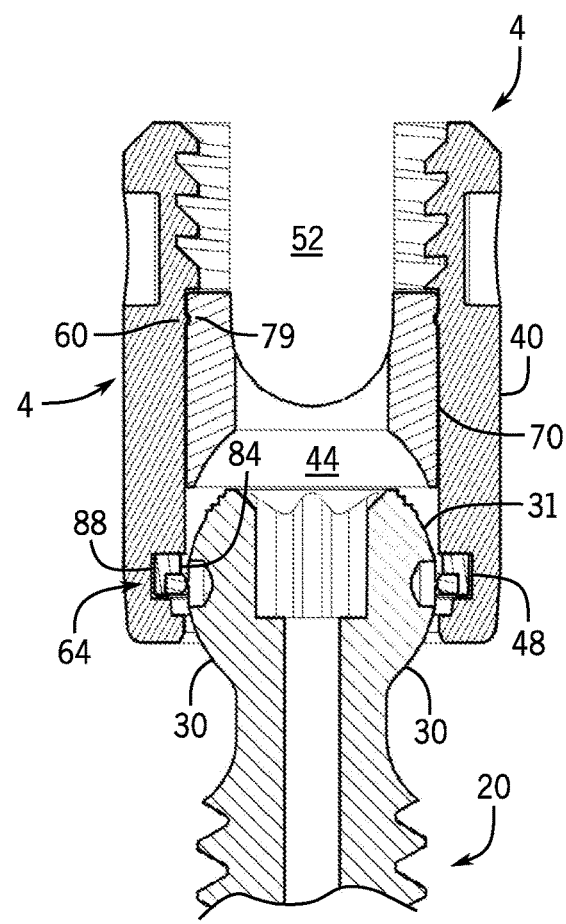
FIG. 19 is a cross-sectional side view of the receiver, insert, positioner, and retainer of FIG. 17, with the shank being further proximally advanced so as to radially expand the positioner and retainer within the receiver expansion chamber.

As shown in FIG. 19, the non-pivoting retainer 90 and positioner 80 have reached a maximum expansion about the shank head 30 at the point where the narrow midline surface 95 of the retainer 90 is situated about the maximum diameter or equator of the spherical head 30 of the shank 20, just prior to capture the shank head within the receiver 40. The cylindrical outer surface 88 of the positioner 80 also approaches the cylindrical inner sidewall surface 64 of the expansion chamber 48.

Figure 20:
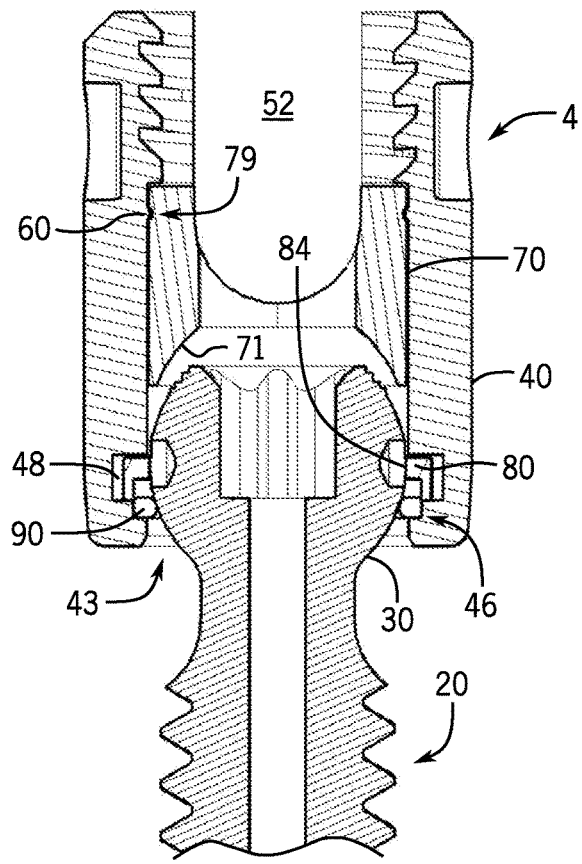
FIG. 20 is a cross-sectional side view of the receiver, insert, positioner, and retainer of FIG. 17, with the shank being further proximally advanced past the positioner and retainer such that the retainer snaps onto a distal side of the head of the shank.

With reference to FIG. 20, the shank head 30 continues to move proximally until the upper inner cylindrical surface 84 of the positioner 80 becomes situated about the maximum diameter or equator of the spherical head 30 of the shank 20, with the retainer moving slightly below the maximum diameter or equator of the spherical head 30 so that the upper inner curvate surface 94 of the retainer 90 presses against lower outer surface 31 of the shank head 30. The angled interface at this position can create a downwardly directed force on the retainer 90 that causes the retainer 90 to release and separate from the positioner 80 and snap downward around the lower portion of shank head 30 as it re-establishes its nominal shape or state. The shank can now be moved or pulled back downward until the retainer 90 enters and positions itself into the locking chamber 46, thereby capturing the shank head 30 with the receiver 40.

At this point the positioner 80, which has also now contracted back into nominal shape, also prevents or limits upward movement of the non-pivoting retainer 90 once the retainer is seated within the locking chamber 46. The positioner 80 stays within the confines of the expansion chamber 48. Therefore, distal or opposite displacement of the shank head 30 fully seats the retainer 90 against the lower annular seating surface 67 and the intermediate cylindrical surface 66 in the lower portion of the retainer bore 44, also known as the locking chamber 46. The seating of the retainer 90 captures and prevents the shank head 30 from exiting the distal or bottom opening 43 in the receiver 40, as the diameter of the shank head 30 exceeds the inner diameter of the retainer seated within the locking chamber 46 that is proximate to the distal opening 43 in the receiver 40. The shank head 30 at this point cannot be pulled out of the receiver 40. The non-pivoting retainer 90 is also stabilized, aligned, constrained, and restrained on the shank head 30 with respect to pivotal, rotational, and elevational alignments by means of the positioner 80. However, as the positioner 80 cannot enter the locking chamber 46, the positioner 80 does not participate in capturing the shank head 30, and only the retainer 90 captures the shank and prevents the shank from exiting the lower opening of the receiver 40. It is foreseen that while the positioner 80 may, in some aspects, include a friction fit with the shank, in such a case the positioner would not prohibit the downward escape of the shank 20, but only serve to restrict upward or proximal movement of the shank.

Figure 21:
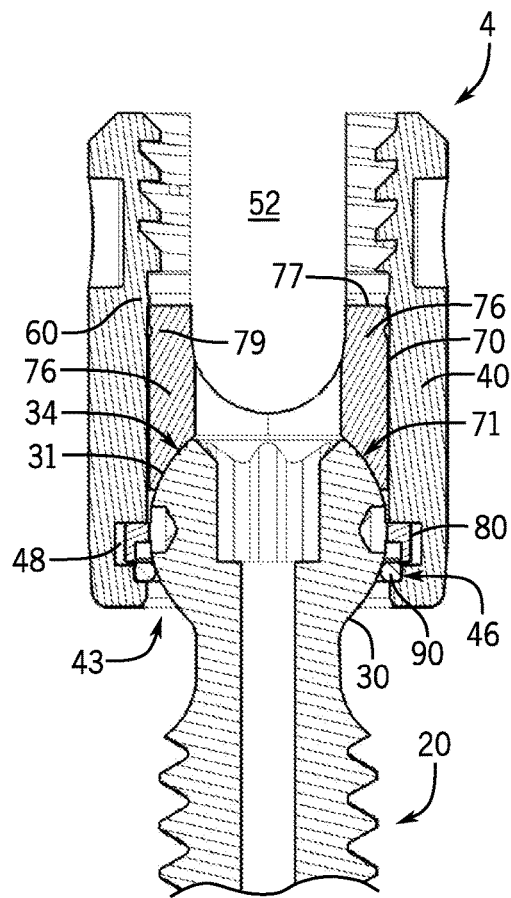
FIG. 21 is a cross-sectional side view of the receiver, insert, positioner, retainer, and shank of FIG. 20, with the insert being distally advanced into engagement with the head end of the shank.

Referring now to FIG. 21, once the shank head 30 is captured, the compression insert 70 is pressed or deployed downwardly by a tool, such as a screw driver (not shown), back toward the shank head 30 and the first axial position described above, in which the top surfaces 77 of the insert upstanding arms 76 once again abut against the rounded bottom portion of the inwardly-projecting discontinuous insert attachment ridge 60. In this configuration, moreover, the distance the insert 70 travels from the second uppermost axial position to the lower first axial position can generally correspond with the distance between the spherical concave engagement surface 71 formed into the bottom face of the insert 70 and the outer surface 31 of the spherical shank head 30. Accordingly, the lower concave surface 71 of the insert can become frictionally engaged with the outer surface 31 of the bone screw shank head 30, without penetration of the insert engagement structures (e.g. upper ridges 34) into the surface of the insert concave surface, so as to create a tight, non-floppy, substantially spherical ball and socket joint between the shank head 30 and the spherical concave surface 71 of the insert 70. The friction fit between the compression insert 70 and the shank head 30 is not totally locked or fixed, but at the same time is not loose or floppy either, advantageously allowing the user to articulate the shank 20 with respect to the receiver 40 by application of manual or tool associated pressure or force, but with some resistance, so that when the shank 20 is placed in a desired orientation with respect to the receiver 40, the bone anchor assembly 1 remains substantially frictionally set in such desired orientation unless purposefully manipulated into another position.

The shank 20 (or an entire bone screw assembly 1 made up of the universal spherical shank 20 with or without, the non-pivoting retainer 90, positioner 80, receiver 40, and compression insert 70) is screwed into a bone or vertebra, by rotation of the shank 20 using a suitable driving tool or tool assembly (not shown) that operably drives and rotates the shank body 22 by engagement thereof at the internal drive or tool engagement structure 36. It is foreseen that the shank 20, the other bone screw assembly parts (also having a central lumen in some embodiments), the rod 10 and the closure top 14 (also with a central bore drive) can be inserted in a percutaneous or minimally invasive surgical manner, utilizing guide wires (not shown) with or without minimally invasive guide tools.

When the shank 20 is driven into the vertebra without the remainder of the bone screw assembly 1, the shank 20 may either be driven to a desired final location or may be driven to a location slightly above the final location or "proud" to provide for ease in assembly with the receiver sub-assembly 4. The pre-assembled receiver 40, insert 70, positioner 80, and non-pivoting retainer 90 can be placed above the shank head 30 until the shank head 30 is received within the distal or bottom opening 43 of the receiver 40.

With reference to FIG. 22, the rod 10 is eventually positioned in an open or percutaneous manner in cooperation with the at least two bone screw assemblies 1. The closure 14 is then inserted into and advanced between the upright arms 50, 51 of the receiver 40. As shown in FIG. 22, the closure 14 can comprise a fastener 15 with a break-off head 16. It will be appreciated, moreover, that the closure 14 can further comprise any of a variety of different types of closure structures for use in conjunction with the present disclosure with suitable mating structure on the upstanding arms 50, 51 of the receiver 40. For example, in one aspect the closure 14 can comprise a nested fastener, such as the nested fastener-type closure described in U.S. patent application Ser. No. 11/140,343, now U.S. Pat. No. 7,776,067, the entirety of which is incorporated by reference herein.

As the closure 14 rotates and moves downwardly into the respective receiver 40, the closure structure 14 can press downwardly against the upper surface of the elongate rod 10 to bias the rod into engagement with the insert 70, thereby urging the shank head 30 toward the lower opening 43 of the retainer 40 and into locking engagement with the non-pivoting retainer 90 that is frictionally abutting the lower annular step or seating surface 67. This downwardly directed force can, in turn, cause the retainer 90 to expand slightly outward to the engage and lock against the intermediate cylindrical surface 66. As shown in FIG. 22, when the shank 20 is articulated at an angle with respect to the receiver 40, both the smooth spherical surface 31 and the stepped upper ridges 34 of the shank head 30 can enter into frictional engagement with the concave spherical surface 71 of the compression insert 70.

II. Multi-Planar or Mono-Planar Bone Screw Utilizing a Spherical Universal Shank with Configurable Coupler With reference to FIGS. 23-53, illustrated therein is another embodiment of the present disclosure comprising a configurable pivotable bone anchor apparatus or assembly 100 that can be selectively configured for multi-planar or mono-planar pivoting motion. It will be appreciated that while the bone anchor for the assembly 100 can generally be a polyaxial bone screw, such as a spherical universal shank 120, the structure and features of the present disclosure could also be utilized with other types of spinal implants that utilize pressure inserts, such as polyaxial bone hooks or clamps, and the like.

As shown in FIG. 23, the selectively configurable multi-planar or mono-planar bone anchor assembly 100 generally includes a spherical universal shank 120 and a receiver sub-assembly 104 that generally includes a receiver 140, a pressure insert 170, a positioner 180, and a retainer ring 190. The bone anchor assembly 100 is generally adapted for use with an elongate rod or connecting member 110 (FIGS. 52, 53), and can also can also include a closure 114 that secures the elongate rod 110 to the receiver sub-assembly 104. Moreover, in this embodiment the spherical universal shank 120 can also be a component of a shank sub-assembly 102 that further includes a coupler 210 or split coupler assembly comprising a pair of collet members 220, a collet lock sleeve 240, and optionally, a pair of ball bearings 250. The coupler 210 can provide for a snap fit between the receiver sub-assembly 104 and the shank sub-assembly 102.

The receiver sub-assembly 104, including the receiver 140, the insert 170, the positioner 180, and the retainer ring 190, may be initially pre-assembled at a manufacturing facility prior to shipping. The shank sub-assembly 102, including the spherical universal shank 210, the collet 220, the collet lock sleeve 240, and optionally the ball bearings 250, 252 may also be initially pre-assembled prior to shipping. Furthermore, the receiver sub-assembly 104 and the shank sub-assembly 102 may be further assembled either prior or subsequent to implantation of the shank 120 into a vertebra (not shown), as will be described in greater detail below.

In some aspects the shank sub-assembly 102 and the receiver sub-assembly 104 can cooperate in such a manner that the receiver sub-assembly 104 and the shank sub-assembly can be secured at any of a plurality of angles, angulation, articulations, or angular alignments relative to one another (i.e. multi-planar motion) and within a selected range of angles from side to side and from front to rear, to enable flexible or articulated engagement of the receiver sub-assembly with the shank sub-assembly until both are locked or fixed with respect to each other near the end of an implantation procedure. In other aspects the bone anchor assembly 100 may be selectively configured or confined to mono-planar motion. In the selectively-configured mono-planar embodiment, for example, the bone anchor assembly may be configured in a sagittal configuration or a transverse configuration.

As with the spherical universal shank included in the first embodiment of the bone anchor apparatus 1 described above, the spherical universal shank 120 depicted in FIGS. 23-25 also includes a shank distal end 121 and a shank proximal end 129 opposite the shank distal end. The shank 120 is elongate, with the shank body 122 having a helically wound bone implantable thread 126 (single or multi start thread forms, which can have various types of thread patterns and cross sections) extending from near the neck 128 to the tip 124 of the body 122 and extending radially outwardly therefrom. During use, the body 122 utilizes the thread 126 for gripping and advancement as it is implanted into the vertebra (not shown) leading with the tip 124 and driven down into the vertebra with a suitable installation or driving tool (not shown), so as to be implanted into the vertebra to up near the neck 128. The shank 120 has a longitudinal axis of rotation 125.

As shown in greater detail in FIG. 25, the proximal end 129 of the spherical universal shank 120 can further include a shank head 130 having a substantially spherically-shaped outer surface 131, with two opposed, co-linear bores 132 extending radially inward from the outer surface 131 toward the longitudinal axis 125 of the shank 120. The radial bores 132 can be closed bores of predetermined diameter and depth, and can have a conically-shaped end walls of pre-determined size and shape. As described in more detail below, the radial bores 132 are generally configured to receive a pair of spherical ball bearings 250 that are operable, in combination with the coupler sub-assembly or coupler 210, to restrict or limit the motion of the spherical universal shank 120 relative to the receiver 140 to mono-planar motion. Absent the ball bearings 250, however, the spherical universal shank 120 is free to move relative to the receiver 140 with polyaxial or multi-planar motion until locked into an angular position or orientation by the final engagement of the rod 110 and closure 114 within the receiver sub-assembly 104.

The shank head 130 can also include a tool engagement structure 136 or drive feature aligned with the longitudinal axis 125 of the shank 120 and extending downwardly or inwardly from the top end 135 of the spherical head 130. In one aspect the top end 135 of the spherical head 130 can further include a plurality of projecting insert engagement structures, such as concentric ridges 134. The insert engagement structures can be configured to engage or dig into the concave bottom surface 171 of the pressure insert 170 (FIG. 29) so as to establish a more secure friction or interference fit between the proximal end 129 of the shank 120 and the insert 170 when the two components are ultimately locked together, as shown in FIGS. 52 and 53.

Figure 26:
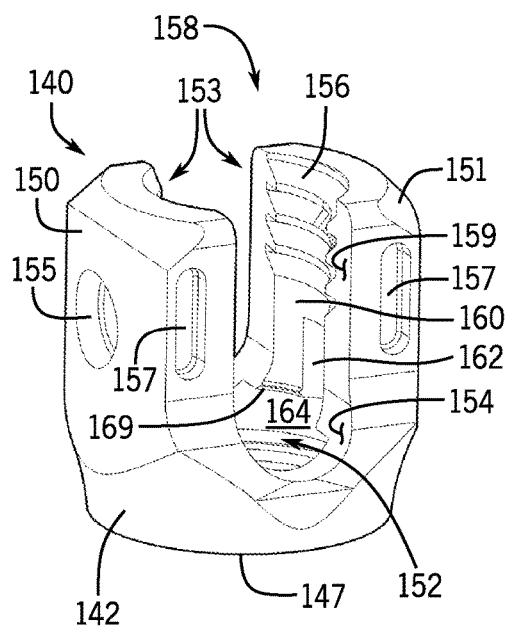
FIG. 26 is a perspective view of the receiver of FIG. 23.
Figure 27:
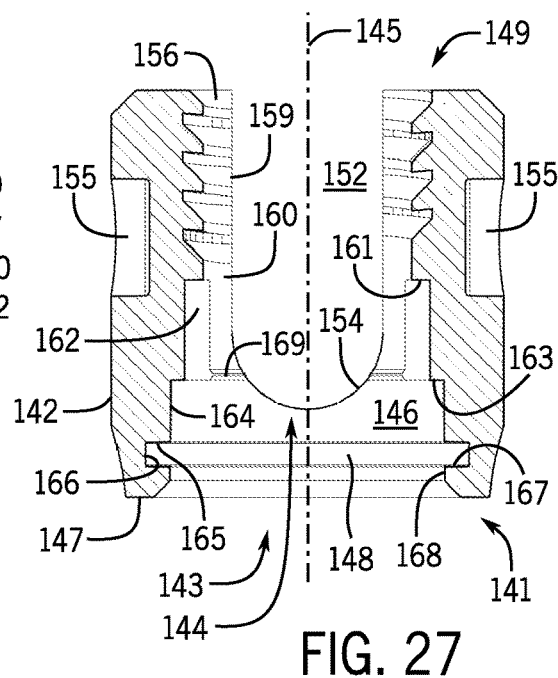
FIG. 27 is a cross-sectional side view of the receiver of FIG. 23.

The receiver component 140 of the receiver sub-assembly 104 is illustrated in detail in FIGS. 26-27, and generally includes a substantially cylindrical base 142 having a central cavity or bore 144 that is centered around a longitudinal axis 145 of the receiver 140. At the distal end 141 of the receiver 140 the bore 144 opens to the bottom surface 147 of the base 142 through bottom or distal opening 143. Integral with the base 142 is a pair of opposed upstanding arms 150 and 151 forming a cradle and defining a channel 152 between the arms 150 and 151 with an upper opening, generally 158, and a U-shaped lower seat 154, the channel 152 having a width for operably receiving the rod 110 between the arms 150, 151, as best seen in FIGS. 52-53. Each of the arms 150 and 151 has an interior surface 153 that includes both inner cylindrical surface 160 and non-cylindrical surface 162 profiles, and a discontinuous partial helically-wound guide and advancement structure 156 located adjacent the top surfaces of each of the arms 150, 151. It is foreseen that the receiver may further include extensions (not shown) attached to the arms 150, 151 having break off junctures to the arms. The breakoff extensions can also have internal threads.

The central bore 144 of the receiver 140 is in communication with the U-shaped channel 152 and can extend upwardly from the bottom or distal opening 143 up to the upper or proximal opening 158. As described in more detail below, the lower portion of the bore 144 can include a cylindrical expansion chamber 148 for receiving the retainer 190 therein, as well as a cylindrical coupler chamber 146 for receiving both the positioner 180 and coupler 210 therein. Above the cylindrical coupler chamber 146 the bore 144 is in communication with the U-shaped channel 152, and can include both the center channel surface 160 and the vertically-directed side recess 162 formed into the inner surfaces 153 of the upstanding arms 150, 151 for slidably receiving at least of a portion of the insert 170 therein.

Figure 52:
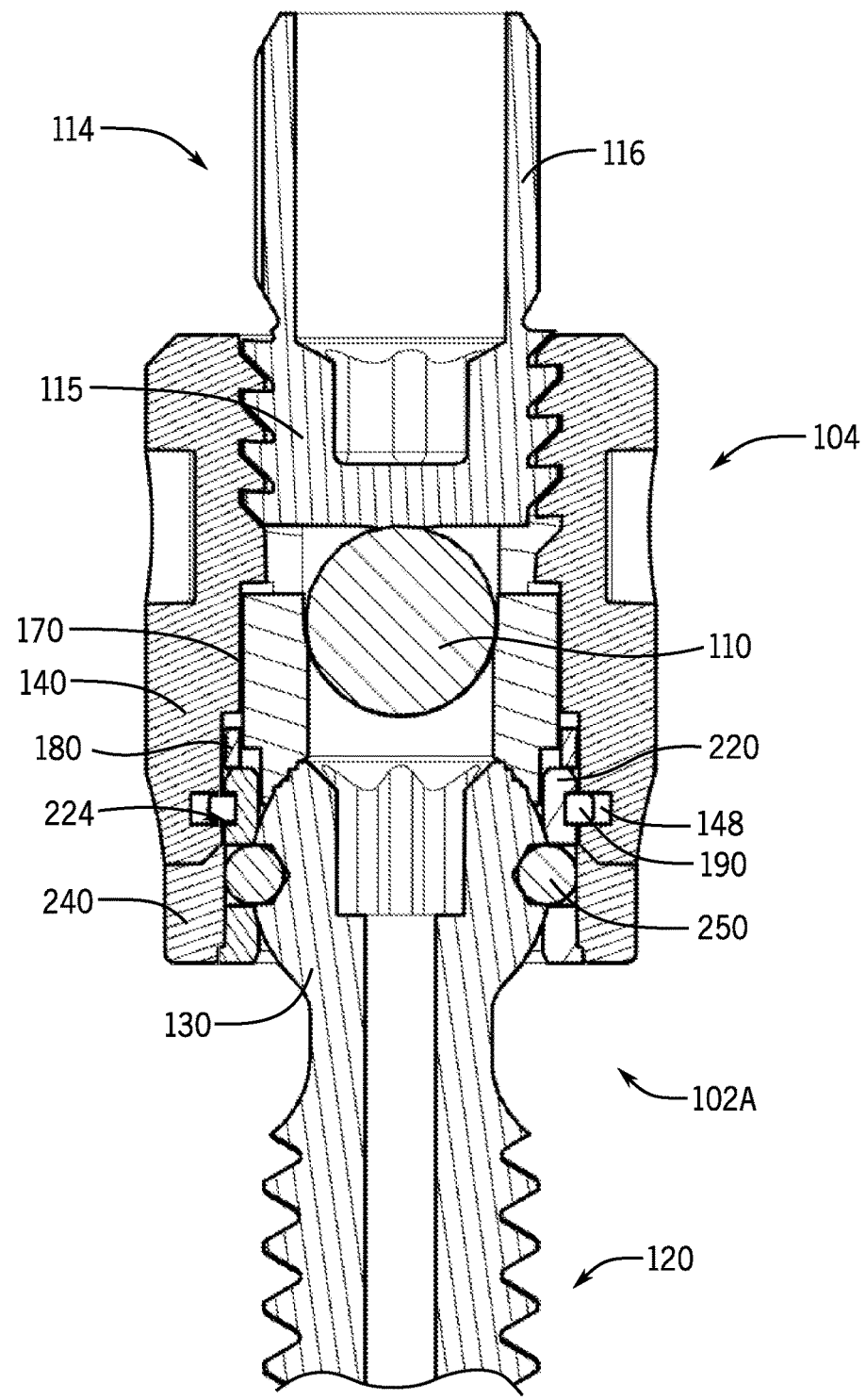
FIG. 52 is a cross-sectional side view of the shank sub-assembly of FIG. 23 with ball bearings secured within the receiver assembly of FIG. 23, and with a connecting member and a closure further locking the shank in a particular mono-planar (into the paper) orientation relative to the receiver.
Figure 53:
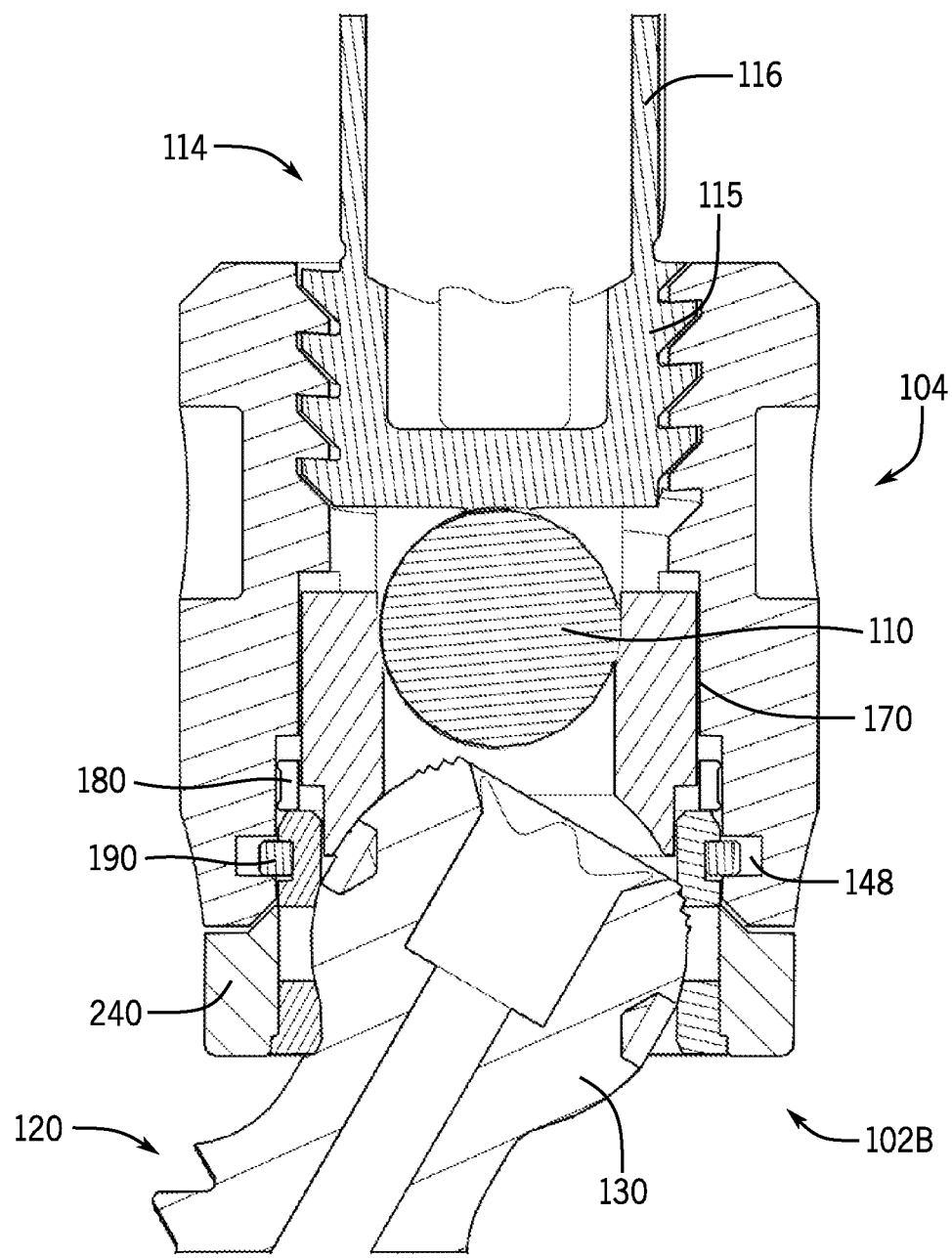
FIG. 53 is a cross-sectional side view of the shank sub-assembly of FIG. 23, without ball bearings, secured within the receiver assembly of FIG. 23, and with a connecting member and a closure further locking the shank in a particular multi-planar orientation relative to the receiver.
Figure 54:
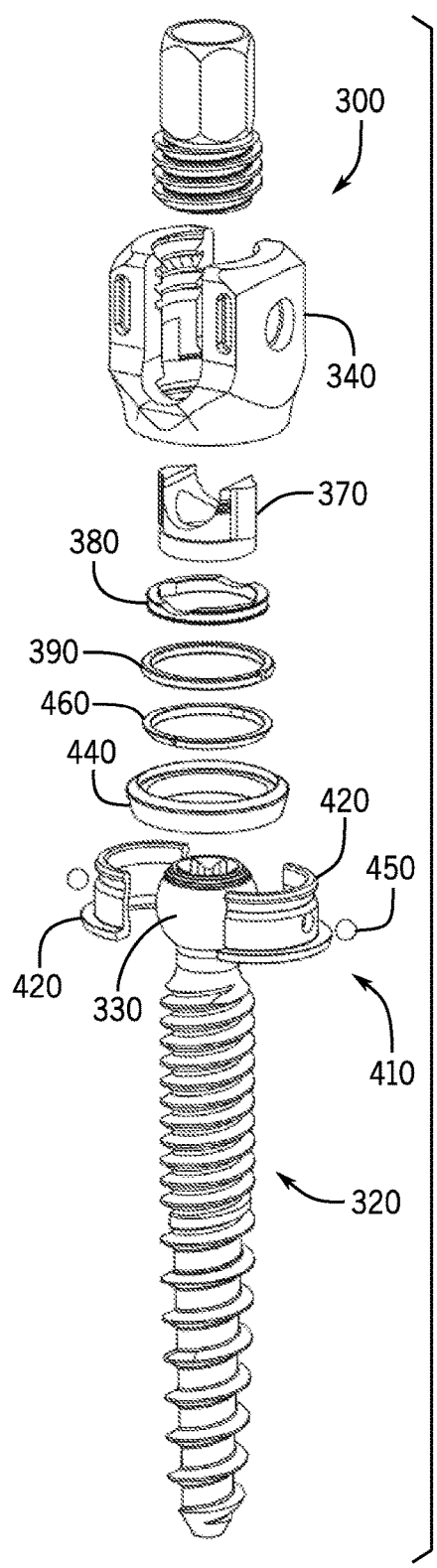
FIG. 54 is an exploded perspective view of a bone anchor assembly, in accordance with another representative embodiment of the present disclosure.

In one aspect the discontinuous guide and advancement structure 156 can be a partial helically wound reverse angle thread form configured to mate under rotation with a similar fastener structure 115 formed into the closure 114 (FIGS. 52-53). However, it is foreseen that the guide and advancement structure 156 could alternatively be a square-shaped thread, a buttress thread, an interlocking flange form or other thread-like or non-thread-like helically wound and non-helically wound discontinuous advancement structure for operably guiding, under complete or partial rotation, and advancing the closure 114 downward between the arms 150, 151, as well as eventual torqueing when a bottom of the closure 114 abuts against the rod 110. It is also foreseen that the closure 114 need not have a breakoff head 116 in certain embodiments.

An opposed pair of first tool receiving and engaging apertures or indentations 155 can be formed into outer side surfaces of the illustrated arms 150, 151. Furthermore, an additional two pairs of second tool receiving and engaging apertures 157 may be formed in front and rear surfaces of the arms 150, 151. Some or all of the apertures 155 and 157 may be used for holding the receiver 140 during the implantation of the shank body 122 (FIG. 24) into a vertebra when the shank is pre-assembled with the receiver 140, and during assembly of the bone anchor assembly 100 with the rod 110 and the closure structure 114. It is foreseen that the tool receiving grooves or apertures 155 and 157 may be configured in a variety of shapes and sizes and be disposed at other locations on the receiver arms 150, 151, such as near the top of the receiver arms in the form of horizontal radiused grooves.

Referring to FIGS. 26-27 and returning to the interior surface 153 of the receiver arms 150, 151, moving downwardly, in a direction toward the base 142, adjacent the guide and advancement structure 156 is the discontinuous cylindrically-shaped center channel surface 160 that is oriented substantially parallel to the receiver longitudinal axis 145, and that is sized and shaped to receive the cylindrical side surfaces 178 of the compression insert 70, as will be described in greater detail below. The cylindrical center channel surface 160 is centrally located between two substantially planar outer channel surfaces 159 that extend between the guide and advancement structure 156 and the front and rear faces (not numbered) of the receiver 140. In turn, centered within each center channel surface 160 is the vertically-directed side recess 162 having an upper stop surface 161. The side recess can be size and shaped to slidably receive the shaped upright arms 176 of the compression insert 170 so as to prevent the insert from rotating within the receiver 140 upon insertion into the bore 144.

An upper shelf or stop surface 163 is located below both the center channel surface 16 and the side recess 162, and is disposed substantially perpendicular to the receiver longitudinal axis 45 to form an upper stop for the positioner 180, prohibiting the positioner 180 from moving upwardly into the upper portion of the bore 144 that receives the compression insert 70. In one aspect the upper stop surface 163 can further define the upper surface of the coupler chamber 46, with cylindrical surface 164 further defining the sidewall surface of the coupler chamber 146 that extends downwardly to an annular shelf or stop surface 165 that extends radially outward from cylindrical surface 164. The upper stop surface 163 and the sidewall cylindrical surface 164 partially define a cylindrical coupler chamber 146 that is sized and shaped to house the positioner 180 and a lower portion of the insert 170 prior to the uploading of the shank sub-assembly to the receiver sub-assembly. The coupler chamber is also sized and shaped to receive the coupler 210 surrounding the spherical head 130 of the shank 120 during uploading, as the shank sub-assembly 102 moves upwardly through the bore 144 during assembly.

Annular shelf or stop surface 165 defines the upper surface of the expansion chamber 148, with cylindrical surface 166 and lower annular shelf or stop surface 167 further defining the sidewall surface and lower surface of the expansion chamber 148, respectively. The lower annular stop surface 167 is also disposed substantially perpendicular to the receiver longitudinal axis 145, and has an inner boundary at a downwardly-extending distal cylindrical surface 168 that defines the distal or bottom opening 143 of the receiver 140. In one aspect the distal cylindrical surface 168 can have a diameter that is substantially the same as the diameter of the cylindrical surface 164 of the coupler chamber 146, allowing for slidable uploading of the compression insert together with the positioner while requiring compression or squeezing of the non-pivoting retainer during uploading into the receiver through the lower opening 43, as described in more detail below. Distal cylindrical surface 168 can be joined or connected to an exterior base surface 147 of the base 142 by one or more beveled, curved or conical surfaces, and defines the bottom opening 143 of the receiver 140.

Furthermore, located between the center channel surface 160 and the upper shelf surface 163 is an insert attachment structure, such as projecting ridges 169, that extend inwardly from the lower interior surface 153 of the receiver arms 150, 151. The projecting insert attachment ridges 169 are spaced apart by the side recess 162 and configured to engage within complimentary receiver attachment groove structures formed into the arms 176 of the insert 170.

Figure 28:
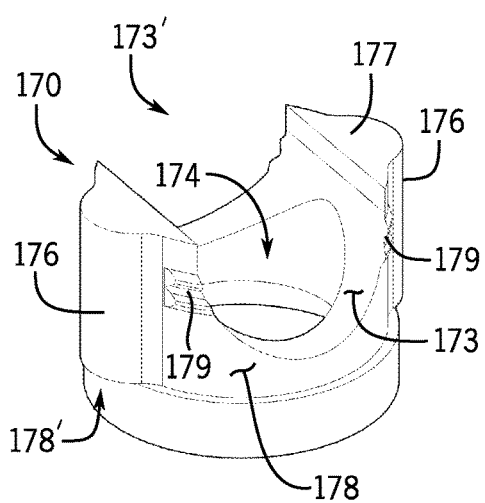
FIG. 28 is a perspective view of the insert of FIG. 23.
Figure 29:
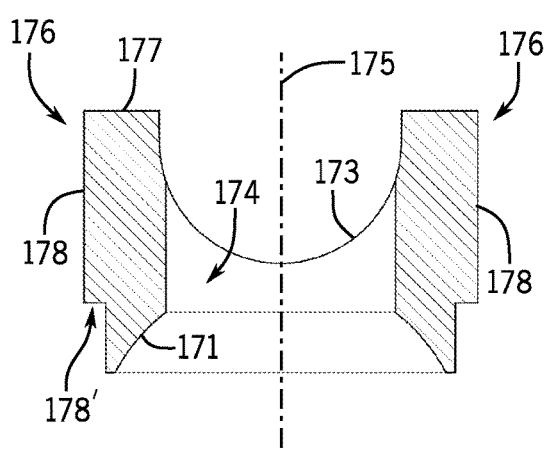
FIG. 29 is a cross-sectional side view of the insert of FIG. 23.

With reference to FIGS. 23 and 28-29, the compression or pressure insert 170 is sized and shaped to be loaded into the bore 144 of the receiver 140 through the bottom opening 143. The illustrated insert 170 has a central axis 175 operationally aligned with the central axis 145 of the receiver 140. In operation, a concave shank head engagement surface 171 formed into the bottom face of the insert 170 advantageously frictionally engages with the outer surface 131 of the bone screw shank head 130, allowing for un-locked, but non-floppy placement of the angle of the shank 120 with respect to the receiver 140 during surgery, prior to locking of the shank 120 with respect to the receiver 140 near the end of the procedure with a rod or connecting member 110 and a closure 114, as shown in FIGS. 52-53. It is foreseen that the insert 170 may be made from a resilient material, such as a stainless steel or titanium alloy, or a polymer, or some combination thereof, so that portions of the insert may be expanded about and then contracted, snapped or popped onto the shank head 130 as well as over the insert attachment ridges 169. Furthermore, in the as-shipped configuration (FIG. 41) the insert 170 is suspended within the receiver 140, being frictionally held in place by the insert attachment ridges 169 projecting inward from the lower inner surfaces 153 of the receiver upright arms 150, 151 (FIGS. 26-27). In this way the insert 170 is prohibited from moving either upward or downward out of the receiver distal opening 143 during shipping and storage, and is held in place until deployment of the insert through the insertion of the shank sub-assembly 102 into the receiver sub-assembly 104.

The illustrated insert 170 generally includes a substantially cylindrically shaped lower body 172 with a pair of spaced apart upstanding arms 176 having top surfaces 177. The inner surfaces of the insert upstanding arms 176 can include proximal-facing saddle or seating surfaces 173 that form a U-shaped insert channel 173' therebetween for receiving and engaging the underside surface of the elongate rod. There is also an axially aligned and centered through bore 174 that runs from the top to the bottom of the insert 170. The bore 174 is defined by an inner cylindrical surface that is at least partially bounded on the upper end by the U-shaped channel seating surfaces 713 and on the lower end by the concave shank head engagement surface 171. The through bore 174 is sized and shaped to receive a driving tool (not shown) therethrough that can engage with the shank tool engagement structure 136 when the shank body is driven into bone with the receiver attached. It is foreseen that the insert shank head engagement surface 171 may comprise a roughened or textured surface or surface finish, or may be scored, grit blasted, knurled, or the like (not shown), for enhancing frictional engagement with the shank head 30.

The center portion of the outer surface of the upstanding arms 176 can be shaped with a curved but non-cylindrical profile that slidably engages with the vertically-directed side recess 162 formed into the interior surface 153 of the receiver arms 150, 151, so as to prevent the insert from rotating within the receiver 140 upon insertion into the bore 144. This ensures that the insert channel 173' is aligned with the receiver channel 152, and with the elongate rod 110 being received by the insert saddle or seating surfaces 173 and spaced from the interior surfaces 153 of the receiver arms 150, 151 by the thickness of the insert upstanding arms 176, as shown in FIGS. 52-53.

As shown in FIG. 28, the upper side surfaces of each arm 176 can further include one or more receiver attachment grooves 179 spaced a predetermined distance from the top surfaces 177 thereof. Each receiver attachment groove 179 can have a width and radius of curvature that is substantially similar to the width and radius of curvature of the complimentary insert attachment ridges 169 projecting inward from the lower inner surfaces 153 of the receiver upright arms 150, 151 (FIGS. 26-27).

Figure 30:
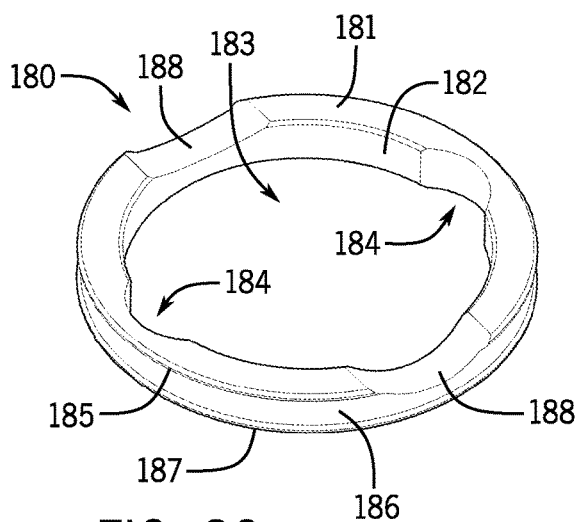
FIG. 30 is a perspective view of the positioner of FIG. 23.
Figure 31:
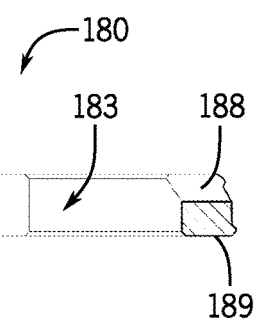
FIG. 31 is a cross-sectional side view of the positioner of FIG. 23.

With reference to FIGS. 23 and 30-31, the positioner 180 can generally comprise a ring-shaped body made from a rigid solid material, such as a stainless steel, titanium alloy, cobalt chrome, or the like, as well as polymers, or some combination thereof, as is generally fixed in both size and shape. The positioner 180 can also have a central axis that is operationally aligned with both the receiver axis 145 and the central axis of the non-pivoting retainer 190, and that may also be aligned with shank axis 125.

The ring-shaped positioner 180 has a central aperture, generally 183, that passes entirely through the positioner body from a top surface 181 to a bottom surface 189 thereof. In one aspect the central aperture 183 can be sized to slide over the cylindrically shaped lower body 172 of the insert 170 with a small clearance. The surfaces that defines the aperture 183 further include a discontinuous inner cylindrical surface 182 that is broken by opposed recesses or cutouts 184 having the same shape or profile as the outer surface of the upstanding arms 176 of the insert 170. This allows the positioner 180 to slide up over the lower body 172 of the insert 170 and into a keyed or "clocked" arrangement with the outer surfaces of the insert arms, so as to prevent relative rotation between the two components.

The positioner 180 further includes an outer cylindrical surface 186 that is also oriented parallel to the positioner central axis. The outer cylindrical surface 186 further includes an upper lip 185 and a lower lip 187 projecting radially outward from the upper and lower edges of the outer cylindrical surface 186 to form a shallow, laterally-directed recess that is sized to capture (or to be capture by) the thickness of the non-pivoting retainer 190 when positioned in the as-shipped configuration (FIG. 41), as described in more detail below. In addition, in one aspect shallow scalloped surfaces 188 can be formed into the top surface 181 of the positioner 180 and orthogonal to the cut-outs 184 formed into the inner cylindrical surface 182, so as to provide additional clearance for the elongate rod 110 or connecting member when the bone anchor assembly 100 is assembled into a final and locked configuration.

Figure 32:
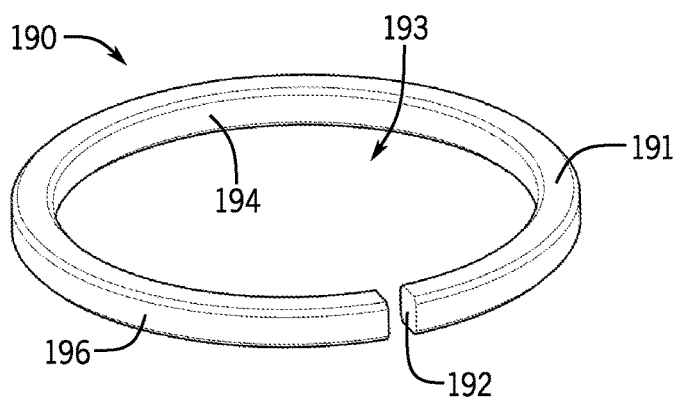
FIG. 32 is a perspective view of the retainer of FIG. 23.
Figure 33:
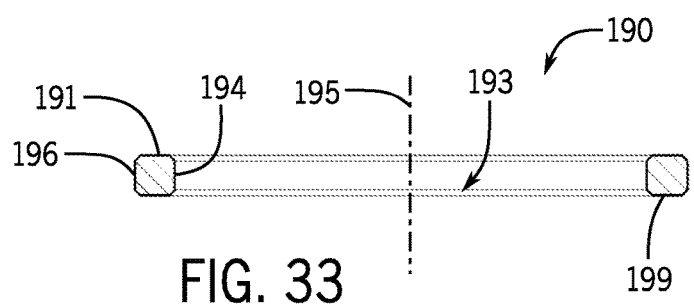
FIG. 33 is a cross-sectional side view of the retainer of FIG. 23.

With reference to FIGS. 23 and 32-33, the non-pivoting retainer 190 can generally comprise an open ring-shaped body made from a resilient material, such as a stainless steel or titanium alloy, cobalt chrome, or the like, or a polymer, or some combination thereof, so that the non-pivoting retainer 190 may be expanded during various steps of assembly, as will be described in greater detail below The non-pivoting retainer 190 has a central aperture 193 that passes entirely through the retainer 190 from a top surface 191 to a bottom surface 199 thereof. The non-pivoting retainer 190 is configured to not pivot with the shank 120 or shank sub-assembly 102, but is situated to ultimately stay within the confines of the receiver expansion chamber 148 (FIG. 27). The central aperture 193 can be defined by an inner cylindrical surface 194 extending between the top surface 191 and the bottom surface 199, and it is foreseen that the inner corners located about either the top surface 191 or bottom surface 199 could be rounded or beveled as needed.

The non-pivoting retainer 190 further includes both an inner cylindrical surface 194 and an outer cylindrical surface 196 extending between the top surface 191 and the bottom surface 199. The outer surface 196 is oriented parallel to the retainer axis 195, and it is foreseen that the outer corners located about either the top surface 191 or bottom surface 199 could also be rounded or beveled as needed. It is also foreseen that two or more evenly spaced notches or bumps (not shown) may be formed in the top surface 191, outer surface 198, or bottom surface 199 to more evenly distribute stress across the entire non-pivoting retainer 190 during contraction and expansion thereof.

The resilient non-pivoting retainer 190 further includes first and second end surfaces 192 disposed in opposed spaced relation to one another when the retainer 190 is in a nominal or neutral state (i.e., without compression or tension). Both end surfaces 192 can be disposed substantially perpendicular to the top surface 191 and the bottom surface 199 and parallel with retainer axis 195. The embodiment shown in FIG. 32 shows the slit or gap between the end surfaces 192 as being substantially parallel; however, it is foreseen that it may be desirable to orient the end surfaces obliquely or at a slight angle, depending upon the amount of compression desired during loading of the non-pivoting retainer 190 into the receiver 140.

Figure 40:
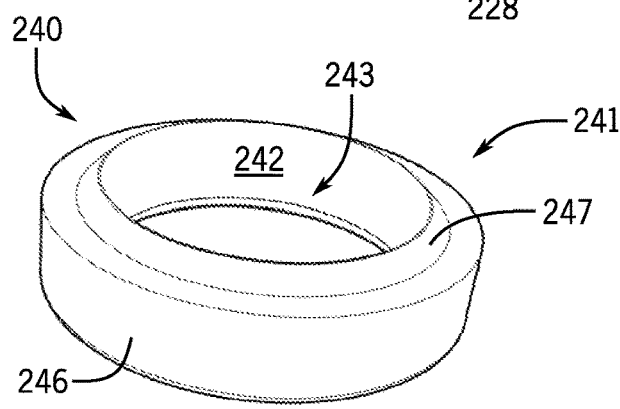
FIG. 40 is a perspective view of the collet lock sleeve of FIG. 23.

A gap of nominal width between the end surfaces 192 can be determined by a desired amount of compressibility of the open non-pivoting retainer ring 190 when loaded into the receiver 140. The gap generally provides adequate space between the end surfaces 192 for the non-pivoting retainer 190 to be pinched, with the end surfaces being compressed toward one another to a closely spaced or even touching configuration, if necessary, to an extent that the compressed non-pivoting retainer 190 is up loadable through the receiver opening 143, as seen in FIG. 40. After passing upward through the retainer bottom opening 143 to the expansion chamber 148, the non-pivoting retainer 190 is allowed to expand or spring back to its nominal and uncompressed collar-like shape. In one aspect the end portions of the retainer 190 adjacent the end surfaces 193 can be overlappingly compressed together in order to reduce the diameter of the retainer 190 to the point that the retainer will fit through the bottom opening 143 in the receiver 140.

FIGS. 34-37 illustrate one representative method for assembling all the separate components of the receiver sub-assembly 104 into an 'as-shipped' configuration, at which the receiver sub-assembly 104 is configured for a simple 'snap-fit' assembly step onto the coupler 210 of the shank sub-assembly 102. In one aspect the pre-assembly of the receiver sub-assembly 4 can take place in a controlled factory or manufacturing setting. FIGS. 48-51 then illustrate the assembly or coupling of the pre-assembled receiver sub-assembly 104 with the pre-assembled shank sub-assembly 102, such as would take place within or near to an operating room setting by a medical professional, such as by a surgical technician or by the surgeon herself. Illustrations of two exemplary final configurations of the assembled bone screw assembly 100 that includes the elongate rod 110 secured within receiver channel 152 by the closure 114, are then provided in FIGS. 52-53.

Figure 34:
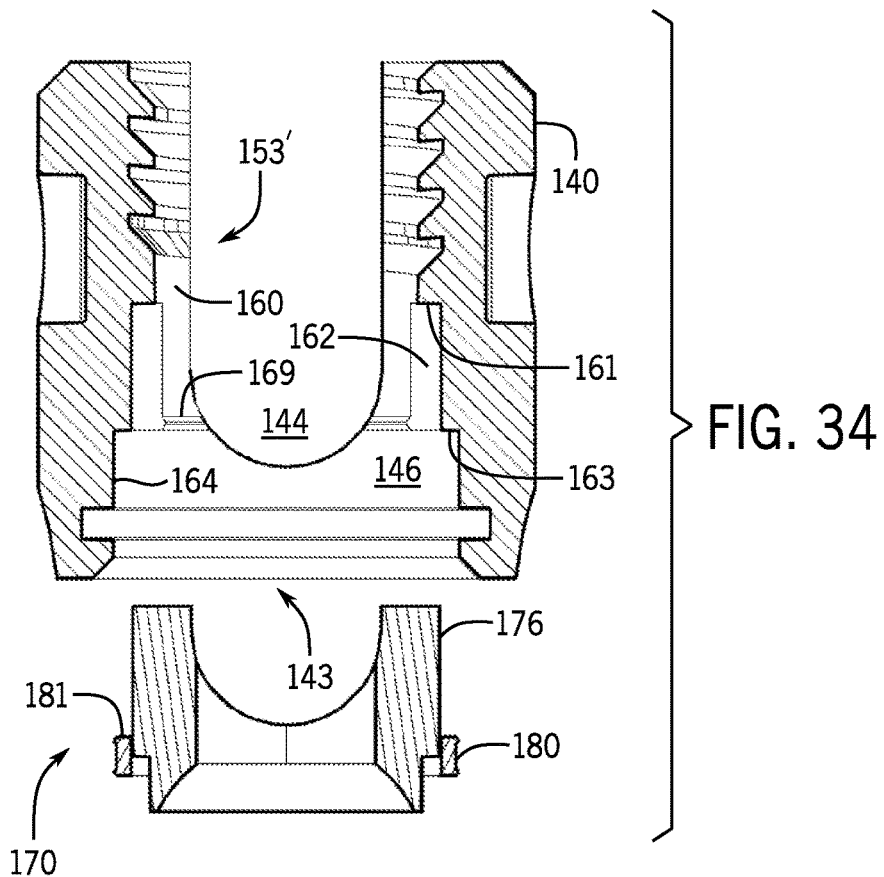
FIG. 34 is a cross-sectional side view of the receiver, the insert, and the positioner of FIG. 23, with the insert and positioner being proximally advanced towards a distal opening of the receiver.
Figure 35:
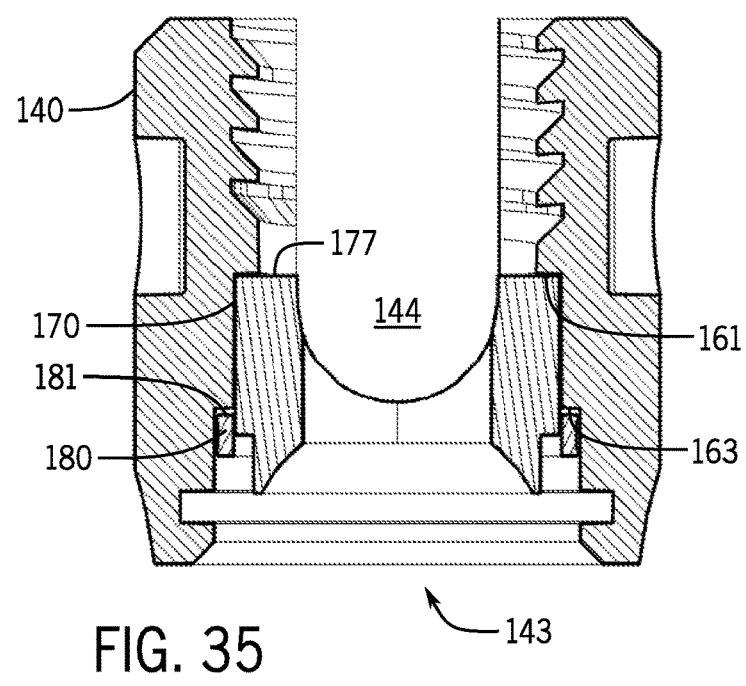
FIG. 35 is a cross-sectional side view of the receiver FIG. 34 with the insert and positioner being seated within the receiver.

With reference to FIG. 34, the positioner 180 can be loosely assembled around the outer surface of the insert 170, with the shaped outer profiles of the insert arms 176 being received into the cutouts 184 (FIG. 30) formed into the inner cylindrical surface of the positioner 180. The two components can then be uploaded together through the bottom opening 143 in the receiver 140 until the insert 170 is received within the upper portion of the bore 144 defined by the center channel surface 160 and the vertically-directed side recess 162 formed into the inner surfaces 153 of the upstanding arms 150, 151, as shown in FIG. 35. In this position the top surfaces 177 of the insert 170 can abut against upper stop surface 161 of the side recess 162 and the top surface 181 of the positioner 180 abuts against upper shelf or stop surface 163 of the coupler chamber 146.

Figure 36:
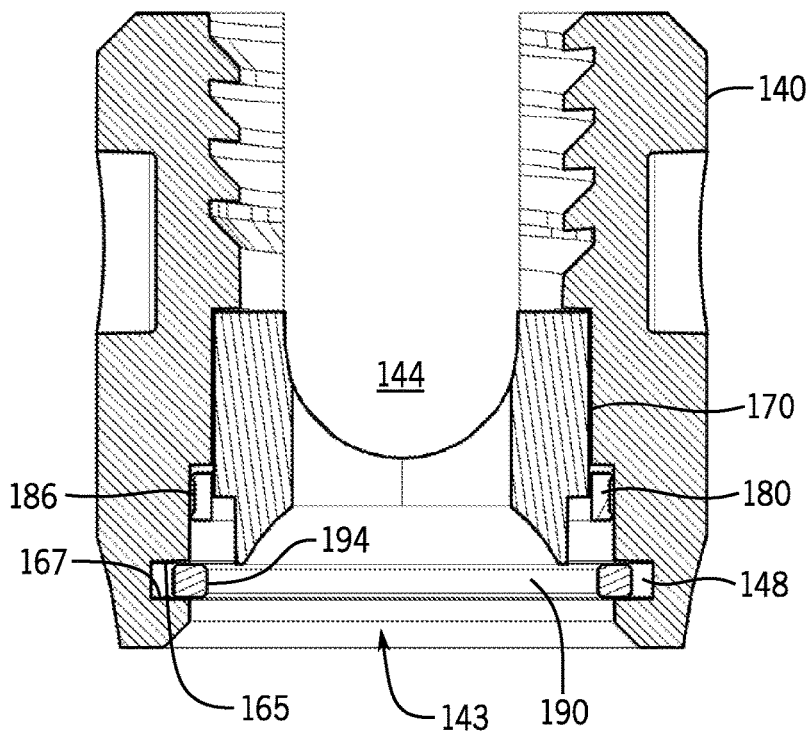
FIG. 36 is a cross-sectional side view of the receiver, insert, and positioner of FIG. 34, with the retainer being proximally advanced through the bottom opening of the receiver and into the receiver expansion chamber.

As shown in FIG. 36, the retainer ring 190 can then be compressed or pinched (e.g. with an external force) as described above, so that its end surfaces 192 approach or overlap each other and its diameter is reduced sufficiently for the retainer 190 to be uploaded through the receiver distal or bottom opening 143 and proximally advanced into the expansion chamber 148, where it is allowed to expand back toward its neutral or nominal size so as to be captured within the expansion chamber 148 by the upper annular shelf or stop surface 165 and the lower annular shelf or stop surface 167 that define the upper and lower surfaces of the expansion chamber 148, respectively.

Figure 37:
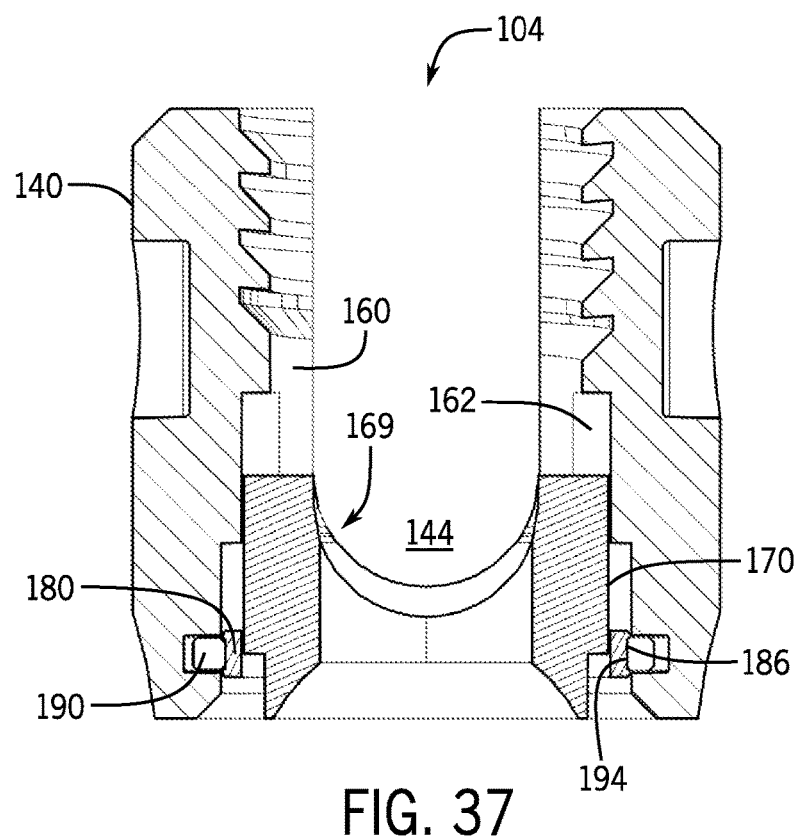
FIG. 37 is a cross-sectional side view of the receiver, insert, positioner, and retainer of FIG. 34, with the insert and positioner being distally advanced so as to engage the retainer and thereby position the retainer and positioner within the receiver expansion chamber to form a receiver sub-assembly in an as-shipped configuration.

As shown in cross-section in FIG. 37, the insert 170 and positioner 180 can then be moved together back downward toward the lower portion of the bore 144 until the receiver attachment grooves 179 (FIG. 28) formed into the upper side surfaces of each insert arm 176 surround and engage with the insert attachment ridges 169 projecting inward from the lower inner surfaces 153 of the receiver upright arms 150, 151 (FIGS. 26-27). With the rounded upper outer portions of the insert arms 176 still received with the complimentary rounded lower portions of the side recesses 162, the upper portion of the insert 170 is securely supported within the bore 144 of the receiver 140.

At the same time the outer cylindrical surface 186 of the positioner 180 becomes engaged with the inner cylindrical surface 194 of the retainer ring 190, thereby pushing the retainer ring further radially outward into the expansion chamber 148. In addition, the upper lip 185 and the lower lip 187 projecting radially outward from the upper and lower edges of the positioner's outer cylindrical surface 186 (FIGS. 30-31) engage with the upper surface 191 and lower surface 199 of the retainer 190. This causes the positioner 180 to become firmly engaged with the retainer 190, with both the positioner 180 and the retainer 190 being centralized within the bore 144 by the lower portion of the insert 170 that is, in turn, secured and centralized within the lower portion of the bore 144, as described above.

With reference now to FIGS. 23 and 38-47, the coupler 210 or split coupler assembly includes a pair of symmetrical half-ring collet members 220, a collet lock sleeve 240, and optionally a pair of ball bearings 250. The collet lock sleeve 240 is configured to press fit the two symmetrical half ring collet members 220 together around the spherical head 130 of the universal spherical shank 120 such that the inner surfaces of the completed split coupler assembly 210 and outer surface 131 of the spherical head 130 have a friction fit arrangement.

Figure 38:
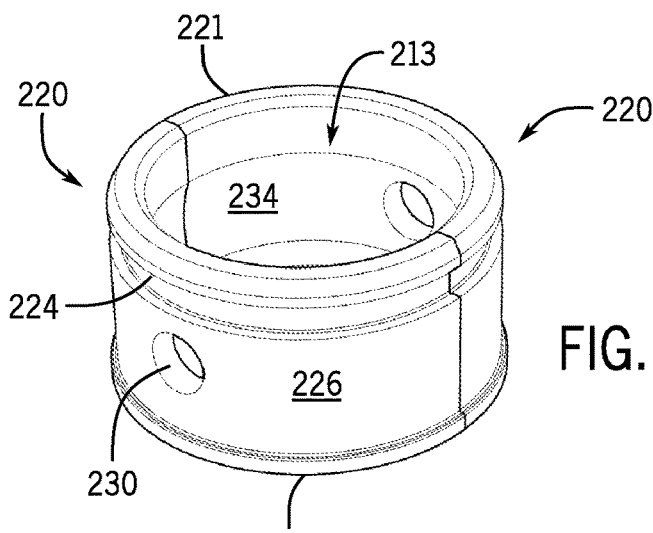
FIG. 38 is a perspective view of the collet members of FIG. 23.
Figure 39:
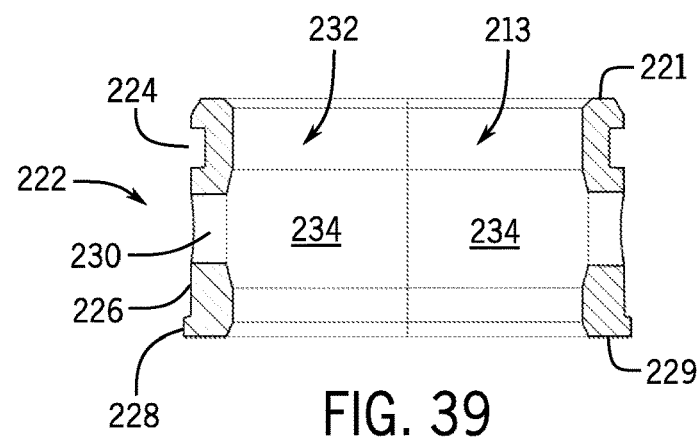
FIG. 39 is a cross-sectional side view of the collet members of FIG. 23.

As shown in FIGS. 38-39, each half ring collet member 220 of the coupler 210 has a top edge or surface 221, a bottom edge or surface 229, and includes an outer surface 222 with a circumferential locking groove 224, a sleeve engagement surface 226 and a lower projecting flange 228 for engaging with a complimentary rabbet groove 249 formed into an inner surface 242 of the collet lock sleeve 240. Each collet member also includes an inner surface 232 with a spherical portion 234 configured to surround and contact the spherical surface 131 of the spherical shank head 130. The collet members 220 may further include opposed spaced apart through bores 230 extending from the outer surface 222 to the inner surface 232, and configured such that the bores 230 of the collet members 220 can be aligned with the bores 132 of the spherical shank head 130 when the combined collet members 220 surround the spherical shank head 130. It will be appreciated that the spherical universal shank 120 and the coupler 210 may be pre-assembled together to form the shank sub-assembly 102.

Figure 41:
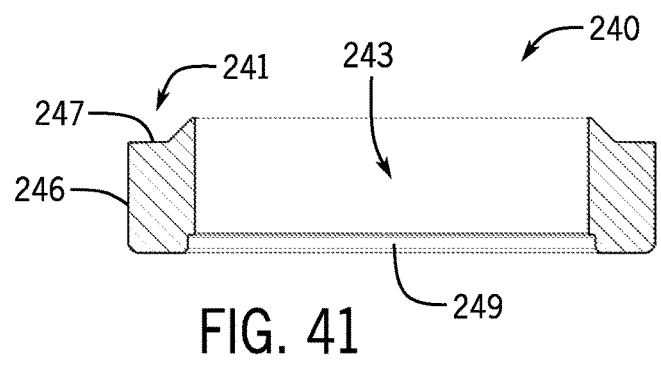
FIG. 41 is a cross-sectional side view of the collet lock sleeve of FIG. 23.

With reference to FIGS. 40-41, the collet lock sleeve 240 generally comprises a solid ring body having an inner surface 242 that defines a through bore 243 extending from the top surface to the bottom surface, and which inner surface can be configured to mate to the sleeve engagement surface 226, in one aspect, with a slight press fit. The upper end surface 241 of the collet lock sleeve 240 can also includes a shaped profile, such as angular profile 247, which is configured to engage with a bottom edge surface of the receiver to form a second rabbet joint that firmly secures the coupler 210 to the bottom of the receiver 140.

Figure 42:
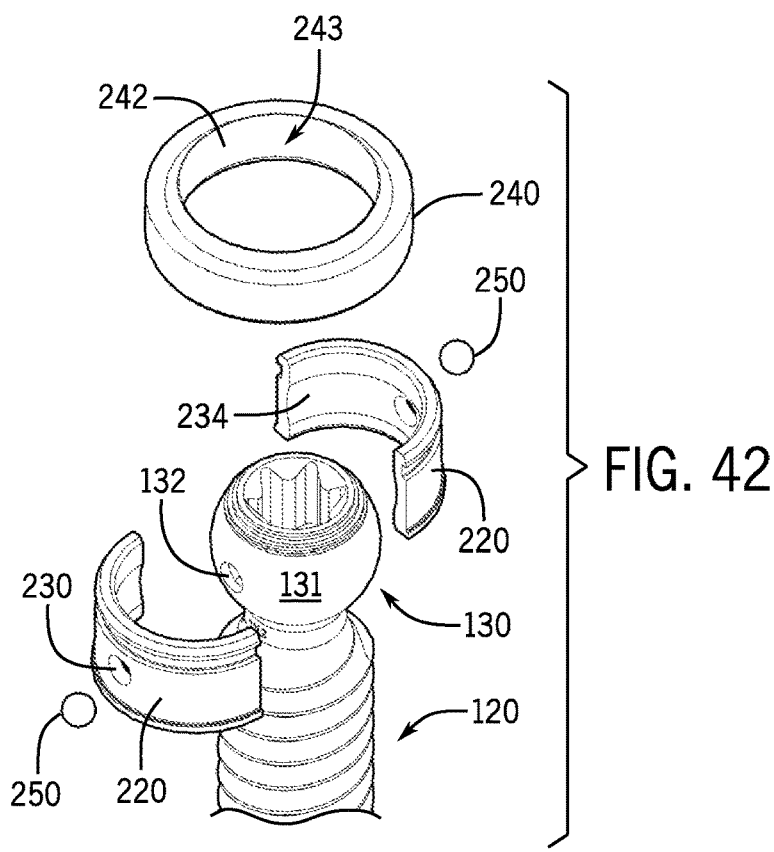
FIG. 42 is an exploded perspective view of the head end of the shank, a pair of collet members, ball bearings, and the collet lock sleeve of FIG. 23.
Figure 43:
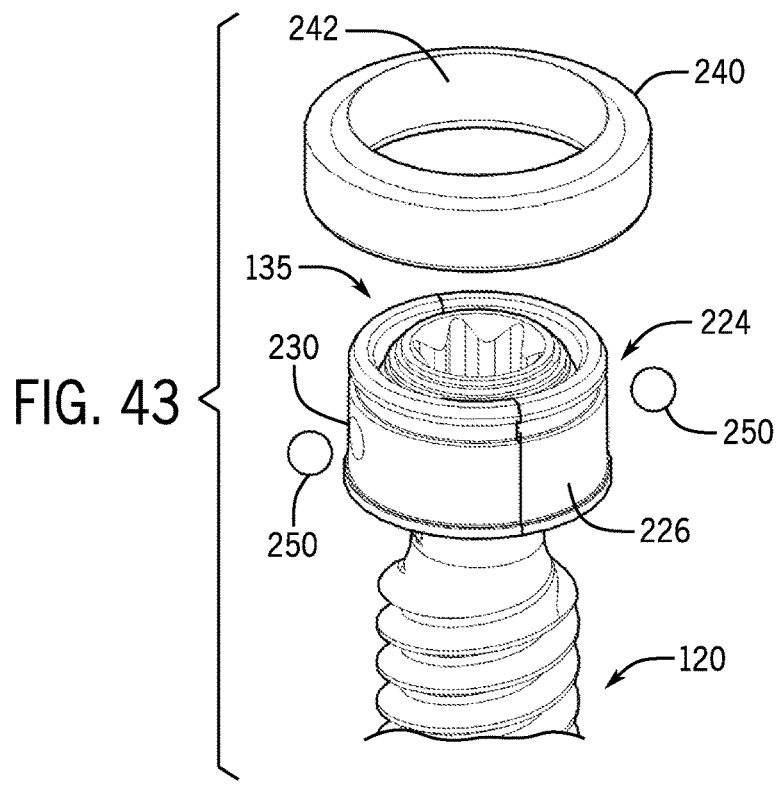
FIG. 43 is a perspective view of the pair of collet members of FIG. 23 fitted to the head of the shank, and the ball bearings and the collet lock sleeve prior to assembly to the collet members.
Figure 44:
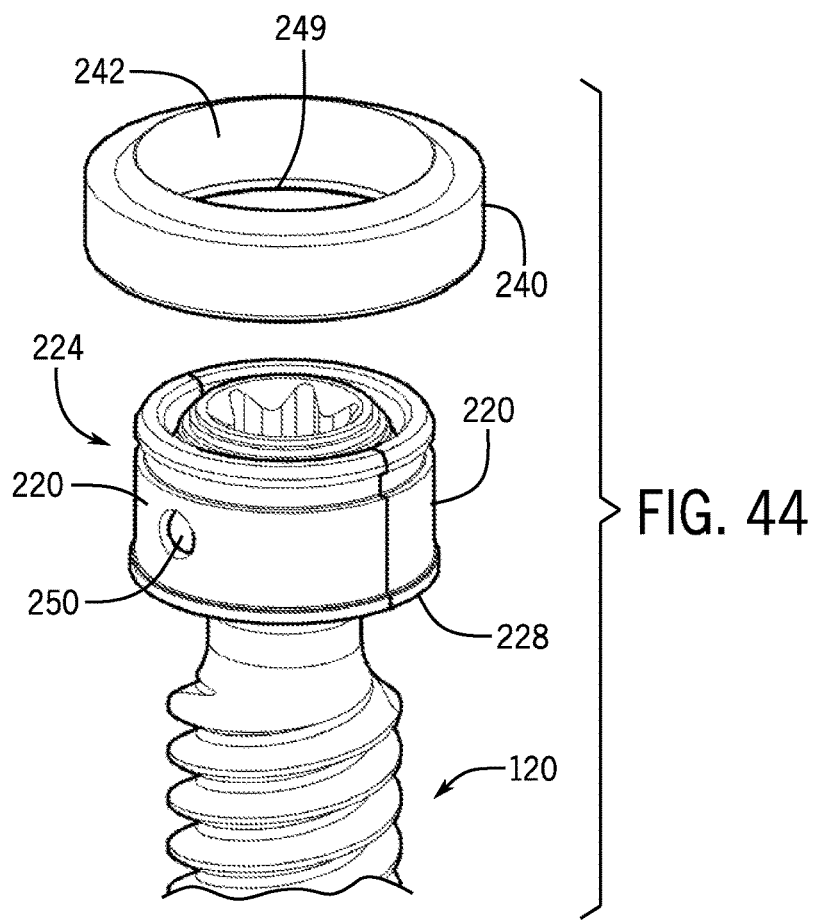
FIG. 44 is a perspective view of the pair of collet members of FIG. 23 fitted to the head of the shank, the ball bearings fitted within openings in the collet members, and the collet lock sleeve prior to assembly around the collet members.
Figure 45:
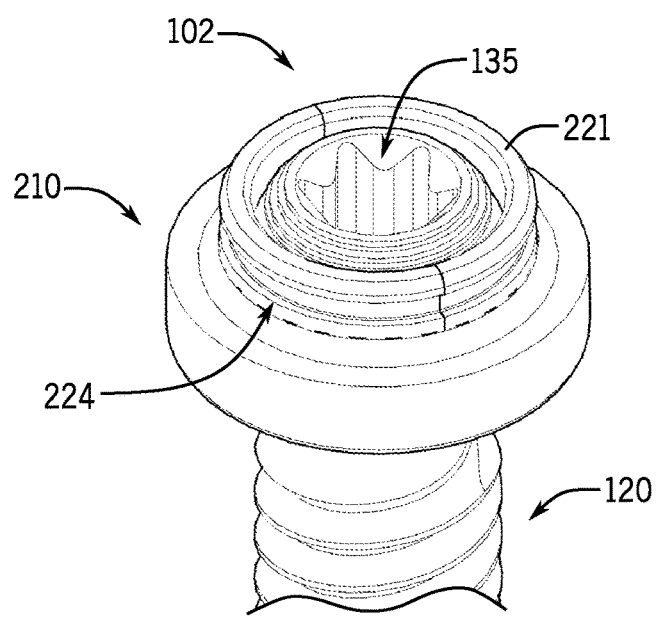
FIG. 45 is a perspective view of the of the assembly shank sub-assembly having the pair of collet members of FIG. 23 fitted to the head of the shank, the ball bearings fitted within openings in the collet members, and the collet lock sleeve fitted around the pair of collet members and ball bearings.

One representative method for assembling the coupler 210 or split coupler assembly around the spherical head 130 of the universal spherical shank 120 is illustrated in FIGS. 42-45. For instance, as shown in FIGS. 42-43, the pair of symmetrical half-ring collet members 220 are first positioned and clamped around the spherical head 130, with the spherical portion 234 of each collet member's inner surface 232 becoming engaged with the spherical surface 131 of the spherical shank head 130. When the engagement between the two spherical surfaces is light, either the clamped-together collet members 220 can be rotated around the head 130 of the shank 120, or the head of the shank can be rotated within the clamped-together collet members 220, until the opposed through bores 230 of the collet members 220 align with the opposed radial bores 132 formed into the shank head 130. As shown in FIG. 44, the ball bearings 250 can then be inserted into the through bores 230 until the outermost surfaces are flush with the outer sleeve engagement surface 226 of the collet members 220.

Once the ball bearing have been installed into the aligned through bores 230/radial bores 132, the collet lock sleeve 240 can be pushed down over the tops 221 of the clamped-together collet members 220 (FIG. 45) until the rabbet groove 249 formed into the collet lock sleeve inner surface 242 becomes engaged with the lower projecting flange 228 to form the first rabbet joint that firmly secures the collet lock sleeve 240 to the clamped-together collet members 220.

As illustrated in FIGS. 46-77, the shank sub-assembly 102A, 102B may be configured to facilitate different movements of the spherical universal shank 120 relative to the receiver sub-assembly (e.g., mono-planar, multi-planar, favored angle, sagittal, transverse) depending on a particular configuration of the coupler 210. In particular, the bone anchor assembly 100 can be configured for multi-planar and mono-planar motion of the universal spherical shank 120 either by excluding or by including the ball bearings 250, respectively, within the bores 132, 230 of the assembled spherical shank head 130 and half ring collet members 220.

Figure 46:
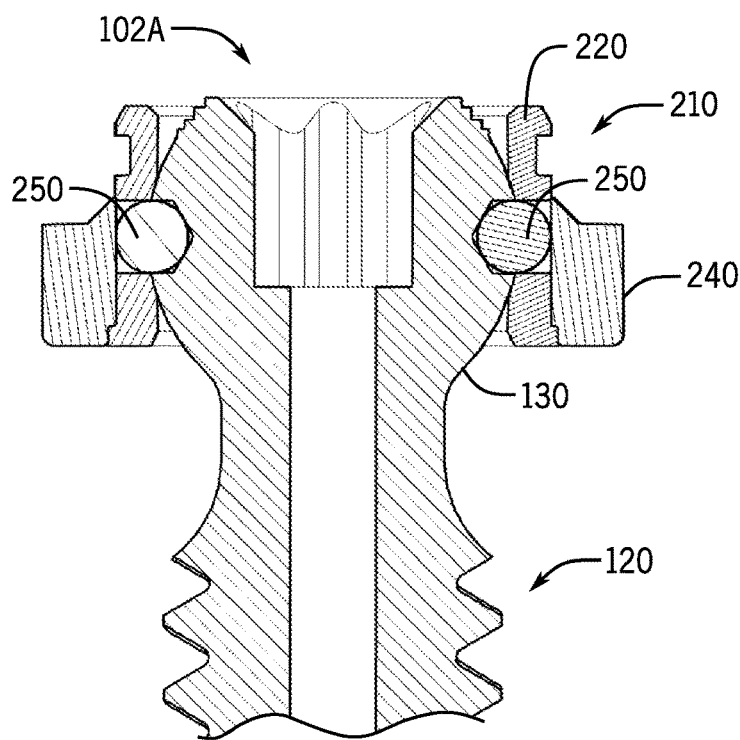
FIG. 46 is a cross-sectional side view of the shank sub-assembly of FIG. 23 with ball bearings.

In one aspect the shank sub-assembly 102A may be configured to facilitate mono-planar motion of the shank 120 relative to the receiver 140. In this mono-planar configuration, the coupler may include the two ball bearings 250, as seen in FIG. 46, that are configured to fit within the bores 230, 132 of the collet 220 and spherical shank head 130 to limit the bone anchor assembly 100 to movement in a single plane. Once the ball bearings are positioned within the coaxially aligned bores of the collet 220 and spherical shank head 130, the collet lock sleeve 240 may be positioned over the ring members 220 of the collet 220 to enclose or securely house the ball bearings in position. With such a design of the coupler may be used to facilitate favored angle configurations, sagittal, and transverse configurations, among others.

Once the ball bearings are positioned within the bores 230 of the collet 220 and coaxially aligned bores 132 of the spherical shank head 130 such that movement of the collet 220 relative to the shank 120 is limited to a single degree of freedom, which is rotation about an axis extending through the ball bearings. With the addition of the ball bearings, all spherical rotation between the shank sub-assembly 102A and receiver sub-assembly is converted to planar motion and all out of plane motion is converted to opposing shear forces against the ball bearings. It is foreseen that other mechanisms may be used instead of ball bearings to limit movement of the shank 120 relative to the collet 220. For example, a pair of cylindrical shafts may be used in place of the ball bearings. As discussed above, FIG. 46 depicts the shipping state or as-shipped configuration of the shank sub-assembly, including the shank 120 and coupler 210 in the mono-planar configuration.

Figure 47:
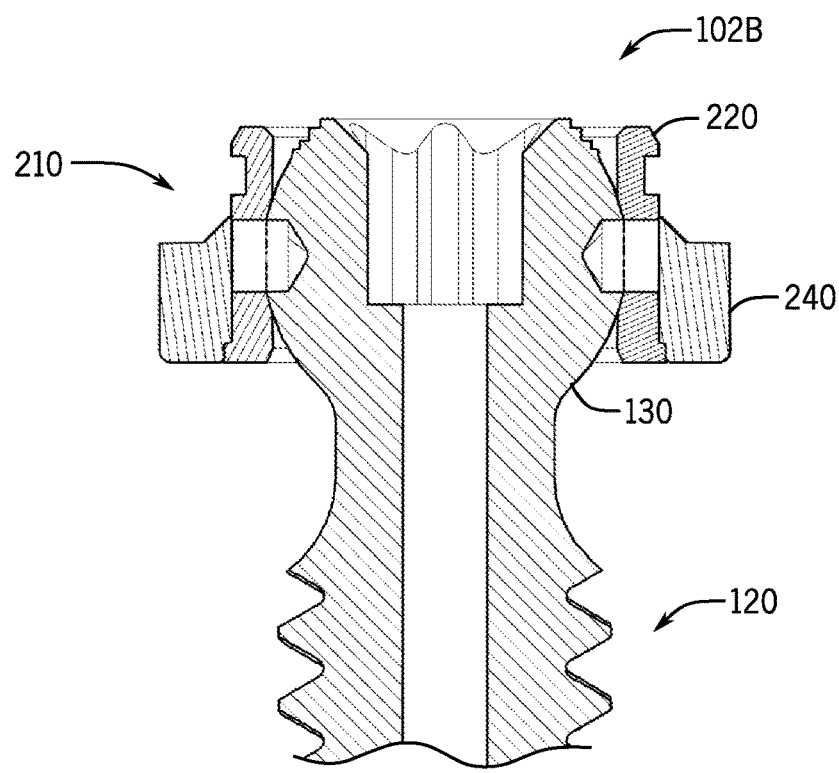
FIG. 47 is a cross-sectional side view of the shank sub-assembly of FIG. 23 without ball bearings.

In another aspect the shank sub-assembly 102B may be configured to facilitate multi-planar motion of the shank 120 relative to the receiver 140. In this embodiment, the bores of the collet 220 and spherical shank head 130 remain empty, as seen in FIG. 47. Leaving the bores empty 230, 132 provides for the spherical shank head 130 to rotate and angulate freely within the collet 220 and receiver sub-assembly until all are locked or fixed relative to each other.

Figure 50:
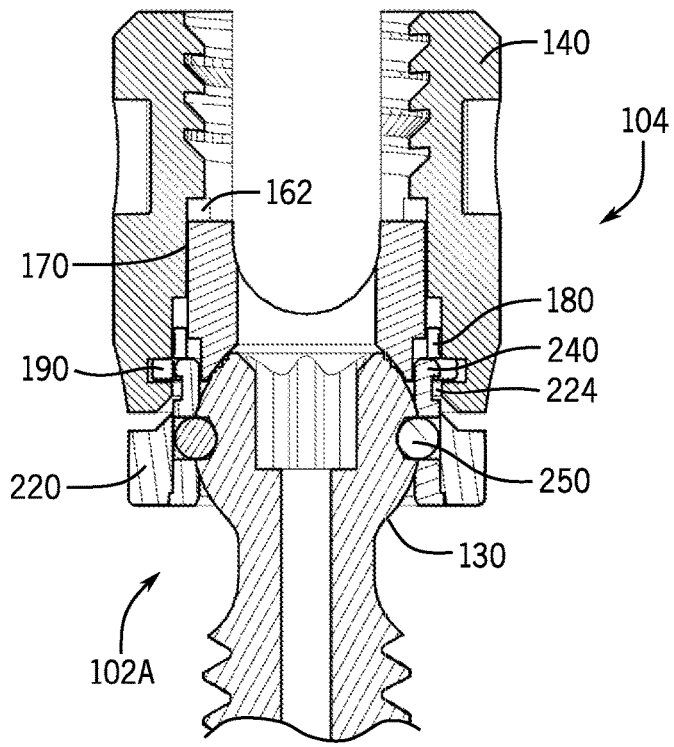
FIG. 50 is a cross-sectional side view of the shank sub-assembly of FIG. 48 with ball bearings being proximally advanced through a bottom opening of the receiver of the receiver sub-assembly.

With reference to FIGS. 48-49, the receiver sub-assembly 104 in the as-shipped configuration may be coupled using a snap-fit arrangement with the shank sub-assembly 102, also in the as-shipped configuration, with the shank subassembly 102 being moved towards the receiver subassembly 104 (or vice versa) so that the coupler 210 approaches the bottom or distal opening 143 of the receiver bore. As seen in FIG. 50, the proximal end of the shank 120 then comes into contact with the distal inner spherical surface 171 of the insert 170 as the shank sub-assembly is forced proximally relative to the receiver 140. This causes the insert 170 to translate or move proximally within the receiver 140. At the same time, the proximal surface 221 of the half-ring collet members 220 of the coupler 210 contacts a distal surface of the positioner 180 and causes the positioner 180 to translate proximally within the coupler or holding chamber 146, as the insert 170 also moves proximally.

Figure 51:
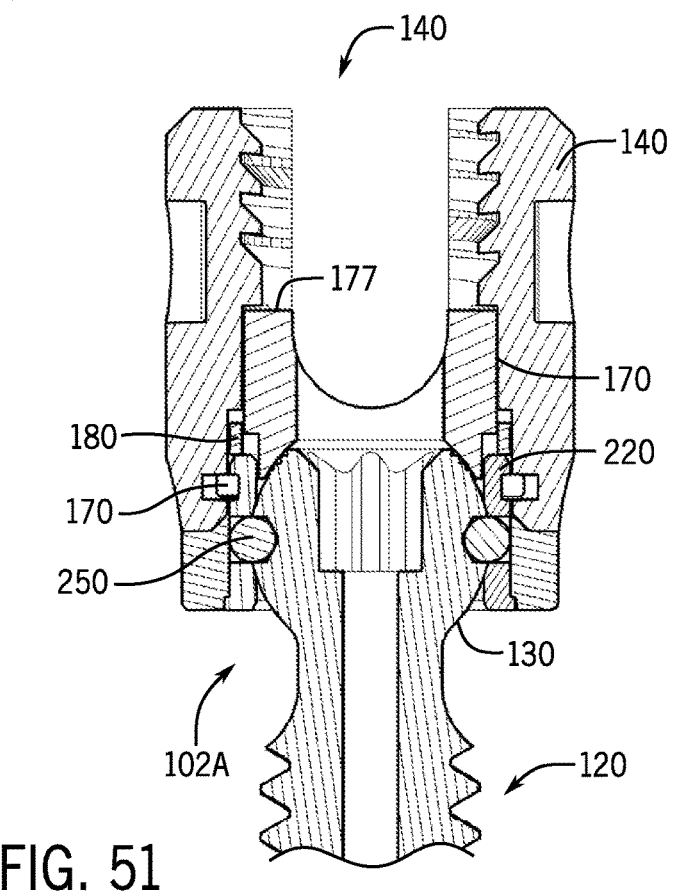
FIG. 51 is a cross-sectional side view of the shank sub-assembly of FIG. 48 with ball bearings being proximally further advanced within the receiver sub-assembly so as to proximally advance the insert and positioner and to allow the retainer ring to become engaged within a locking groove of the collet members.

As the shank sub-assembly 102 is further translated proximally, the retainer ring 190 snaps into the locking groove 224 on the ring members 220 of the collet 220. As seen in FIG. 51, the retainer ring 190 is positioned within the expansion chamber 148 and is constrained from proximal and distal movement by the opposing distal and proximal walls of the chamber 148. And, once the retainer ring 190 is positioned within the locking groove 224 of the half-ring collet members 220 of the coupler, the coupler and shank 120 are also prevented or restrained from distally displacing relative to the receiver 140.

At this point, as seen in FIG. 52, a rod may be positioned within the U-shaped channel 152, 173' of the receiver 140 and insert 170, respectively, and a closure 114 may be threadably engaged with the receiver 140 to secure a distal force on the rod, which in turn, is forced against the proximal cylindrical surface 173 of the insert 170. As described above, with the ball bearings 250 pre-positioned within the coupler 210 of the shank sub-assembly 102A, the motion of the shank 120 is limited to mono-planar motion (i.e. into and out of the plane of the paper) with respect to the receiver 140.

Moreover, and as also described above, when the ball bearings are absent from the coupler of the shank sub-assembly 102B (as seen in FIG. 53), the motion of the shank 120 is not limited to mono-planar motion, and may instead pivot with respect to the receiver 140 with a multi-planar or polyaxial motion.

As illustrated in FIGS. 54-60, the bone anchor assembly 300 may further include a bone clearing mechanism or ring 460 to prevent biological material from entering and clogging certain portions of the assembly. During a spinal surgical procedure, for example, when the shank is implanted into a vertebra, bone debris may fill the circumferential locking groove 424 on the outer surface of the half-ring collet members 420. In one embodiment, the shank sub-assembly 302 may include a bone clearing ring 460 to protect the circumferential locking groove 424 from bone debris during implantation. The collet lock sleeve 440 may further include an inner surface with a circumferential notch 448.

Figure 58:
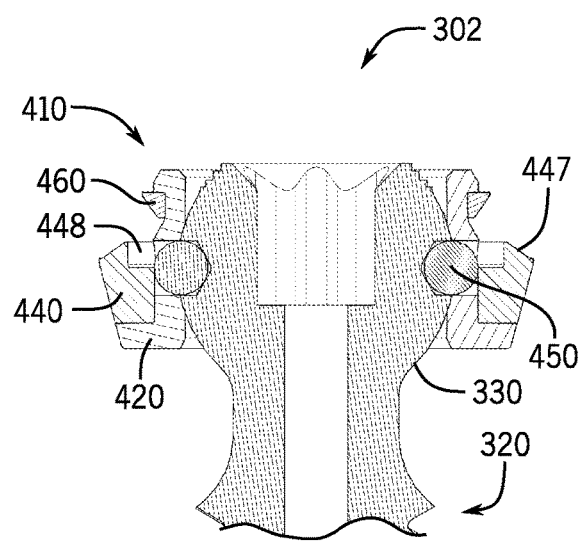
FIG. 58 is a cross-sectional side view of the shank sub-assembly and receiver sub-assembly of FIG. 54 with ball bearings and the bone clearing ring.
Figure 55:
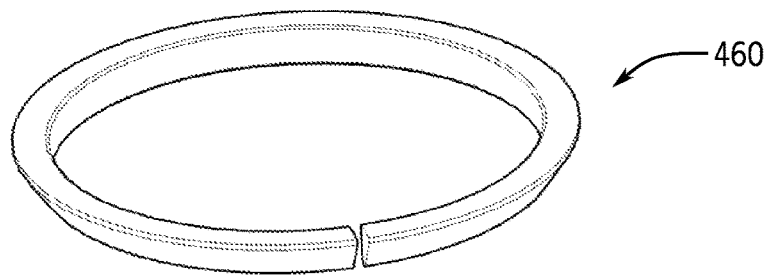
FIG. 55 is a perspective view of the bone clearing ring of FIG. 54.
Figure 56:
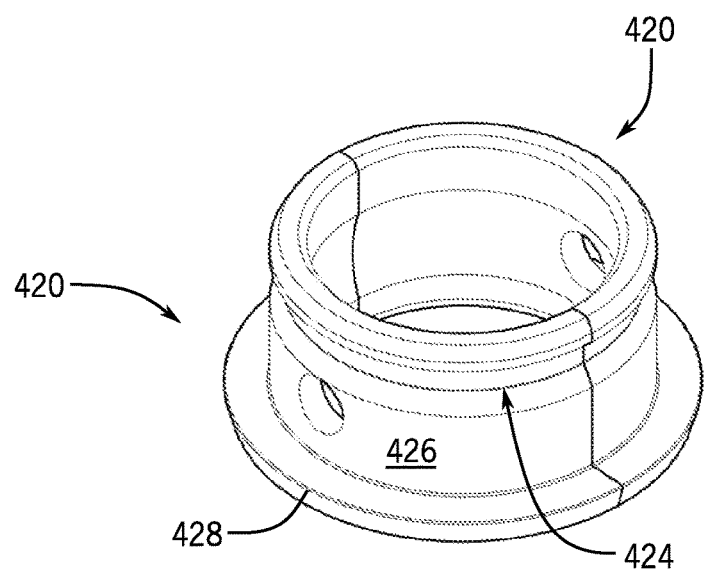
FIG. 56 is a perspective view of the pair of collet members of FIG. 54.
Figure 57:
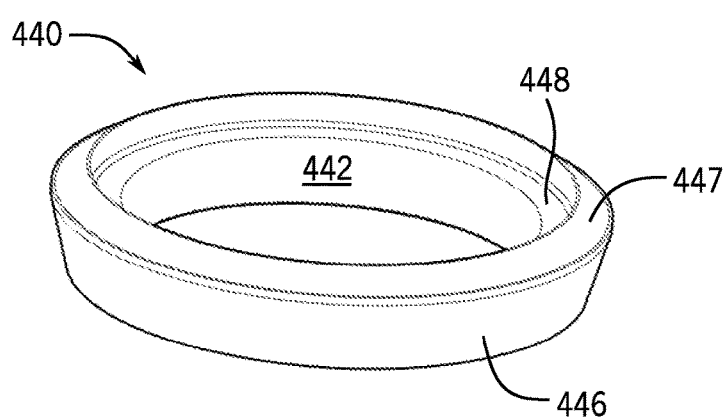
FIG. 57 is a perspective view of the collet lock sleeve of FIG. 54.
Figure 59:
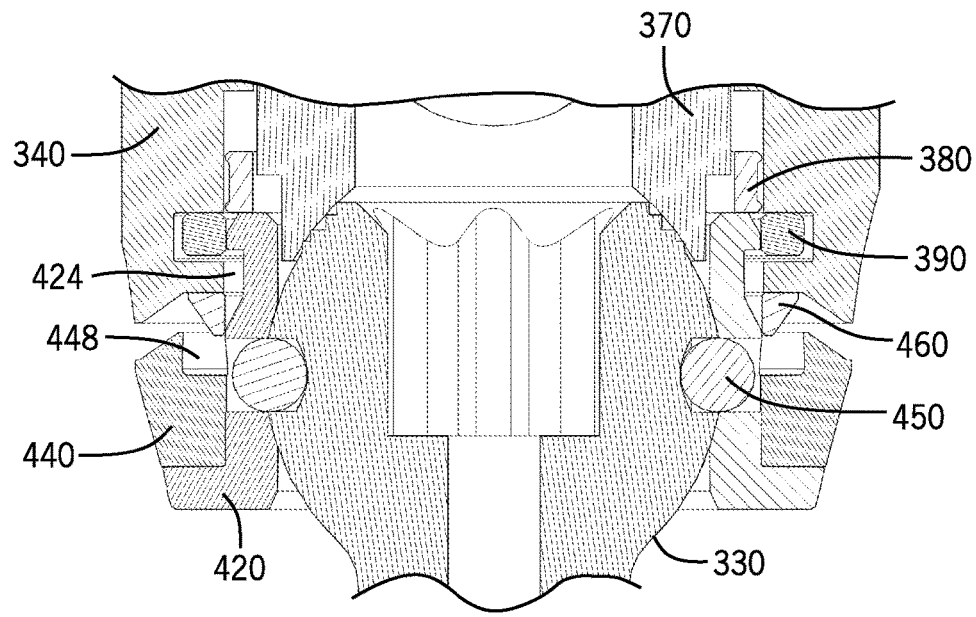
FIG. 59 is a cross-sectional side view of the shank sub-assembly and receiver sub-assembly of FIG. 54 with the bone clearing ring being moved downwardly by the distal end of the receiver as the shank sub-assembly is being proximally advanced through the bottom opening of the receiver.
Figure 60:
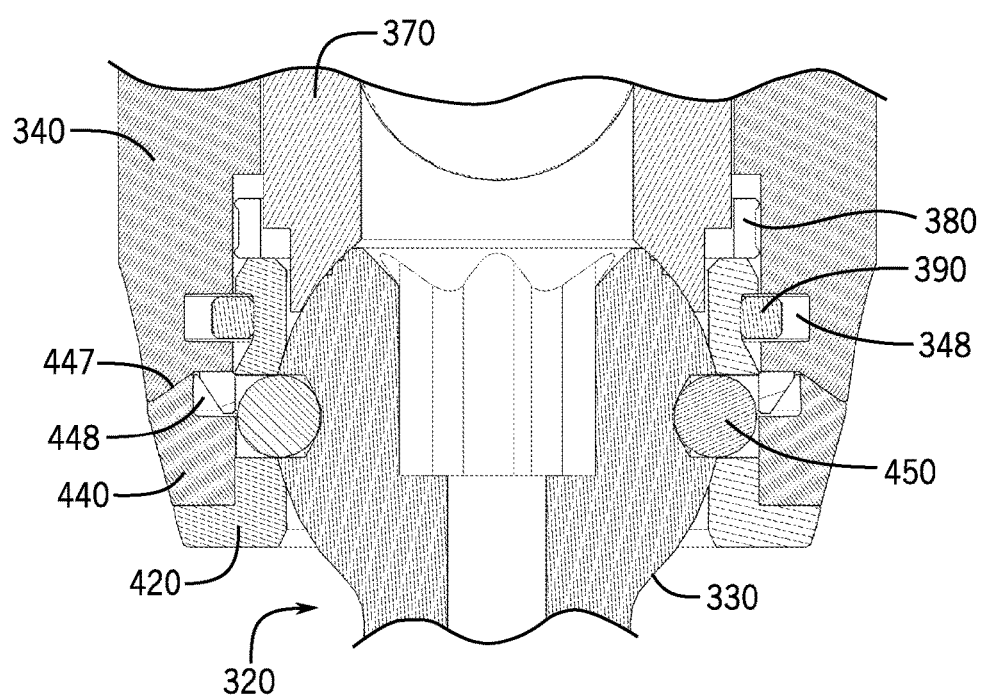
FIG. 60 is a cross-sectional side view of the shank sub-assembly and receiver sub-assembly of FIG. 54 with the bone clearing ring being moved into the circumferential notch of the collet lock sleeve as the shank sub-assembly is being secured within the bottom opening of the receiver.

Prior to installation, the bone clearing ring 446 is configured to be positioned within the circumferential locking groove 424 of the half-ring collet members 420, as seen in FIG. 58. When the shank sub-assembly 302 is at least partially received in the opening of the receiver sub-assembly 304, the bone clearing ring 460 is pushed distally into the circumferential notch 448 in the collet lock sleeve 440 by the distal surface of the receiver 340, as see in FIG. 59. Once in the circumferential notch 448 of the collet lock sleeve 440, the bone clearing ring 460 may abut the ball bearing 450, if present, on one side and the distal surface of the receiver 340 on an adjacent side.

It is noted that the various components of the bone anchor assemblies described herein may include dissimilar metals selected for parts in mutual contact with each other to encourage component penetration under locking conditions.

While embodiments of the bone anchor assemblies described herein include non-pivoting retainers (i.e., the retainer rings do not pivot with the shank relative to the receiver), it is foreseen that the bone anchor assemblies may include pivoting retainers, such as those described in PCT/US15/56706, which is incorporated by reference in its entirety into the present application.

As indicated above, the invention has been described herein in terms of preferred embodiments and methodologies considered by the inventor to represent the best mode of carrying out the invention. It will be understood by the skilled artisan, however, that a wide range of additions, deletions, and modifications, both subtle and gross, may be made to the illustrated and exemplary embodiments of the composite substrate without departing from the spirit and scope of the invention. These and other revisions might be made by those of skill in the art without departing from the spirit and scope of the invention that is constrained only by the following claims.

What is claimed is:

1. A pivotal bone anchor assembly for securing an elongate rod to a bone, the pivotal bone anchor assembly comprising:
    a shank comprising a longitudinal axis, a head, and a body extending distally from the head for anchoring to the bone, the head having an at least partial spherical outer surface with a hemisphere diameter defined as a maximum diameter in a plane perpendicular to the shank longitudinal axis;
    a receiver comprising a longitudinal axis, a proximal end portion, a distal end portion formed integrally with and opposite the proximal end portion, an open channel at the proximal end portion adapted to receive therein the elongate rod, a cavity formed in the distal end portion and proximally opening into the open channel as part of a central bore centered about the receiver longitudinal axis and extending between the distal and proximal end portions, a bottom opening defined in the distal end portion and proximally extending into the cavity, the cavity including an upper expansion chamber and a lower locking chamber;
    a positioner located in the receiver cavity upper expansion chamber and including a gap providing for expansion about the receiver longitudinal axis; and
    a retainer engaged with and held by the positioner at substantially the same level as the positioner in the receiver cavity upper expansion chamber, so as to be stabilized and centralized about the receiver longitudinal axis prior to and during an engagement with the shank head, the retainer being expandable with the positioner about the receiver longitudinal axis,
    wherein, when the shank head enters into the receiver cavity via the bottom opening and is increasingly proximally displaced against the retainer, the shank head increasingly expands the retainer until the hemisphere diameter reaches the level of the retainer, with the expansion of the retainer expanding the positioner, and
    wherein, upon the shank head hemisphere diameter proximally passing the retainer, the retainer disengages from the positioner and self-contracts to move distally along the shank head within the receiver cavity to reach the lower locking chamber, so as to capture and prevent the shank head from distally exiting the receiver cavity via the bottom opening.

2. The pivotal bone anchor assembly of claim 1, wherein after the disengagement of the retainer from the positioner, the positioner is configured to self-contract about the shank head to establish a friction fit between the shank head and the positioner.

3. The pivotal bone anchor assembly of claim 1, wherein the expansion chamber defines a circumferential recess in an interior wall surface of the receiver cavity.

4. The pivotal bone anchor assembly of claim 1, wherein the retainer remains spaced apart from an interior wall surface of the receiver cavity upper expansion chamber throughout the proximal displacement of the shank head.

5. The pivotal bone anchor assembly of claim 1, wherein the expansion of the retainer by the increasingly proximally displacement of the shank head forces the retainer to expand the positioner within the receiver cavity upper expansion chamber.

6. The pivotal one anchor assembly of claim 1, wherein the positioner further comprises an open ring shape with the gap allowing the positioner to be compressible and expandable about a neutral position.

7. The pivotal bone anchor assembly of claim 1, wherein the retainer is ring shaped and includes a gap in its circumference such that the retainer is circumferentially discontinuous to allow for expansion by the shank head.

8. The pivotal bone anchor assembly of claim 1, wherein the receiver cavity lower locking chamber further comprises a proximally facing step surface extending radially from the bottom opening.

9. The pivotal bone anchor assembly of claim 8, wherein the retainer nests against the proximally facing step surface in preventing the shank head from distally exiting the receiver cavity via the bottom opening.

10. The pivotal bone anchor assembly of claim 1, wherein the retainer does not tilt relative to the receiver longitudinal axis when the shank head pivots relative to the receiver.

11. The pivotal bone anchor assembly of claim 1, further comprising an insert positionable within the receiver.

12. The pivotal bone anchor assembly of claim 11, wherein an interference fit between an outer surface of the insert and an inner surface of the receiver maintains the insert in the receiver between the proximal end portion and the distal end portion.

13. The pivotal bone anchor assembly of claim 12, wherein the interference fit is a male/female interference arrangement between the outer surface of the insert and the inner surface of the receiver.

14. A pivotal bone anchor assembly for securing an elongate rod to a bone, the bone anchor assembly comprising:
    a shank including a longitudinal axis, a head, and an elongated body extending distally from the head, the elongated body configured to be received in, and anchored to, the bone, and the head including an at least partial spherical outer surface with a hemisphere diameter defined as a maximum diameter in a plane perpendicular to the shank longitudinal axis;
    a receiver including a proximal end, a distal end opposite the proximal end, a channel that opens at the proximal end and is adapted to receive therein the elongate rod, a central cavity proximally opening into the channel, a distal opening defined in the distal end and proximally extending into the central cavity, and a longitudinal axis that extends between the distal and proximal ends and about which the channel, central cavity, and distal opening are centered;
    a positioner located in the central cavity and radially expandable about the receiver longitudinal axis, the positioner including a distally facing recess extending along an inner boundary of the positioner; and a retainer positioned in the central cavity by the positioner and radially expandable about the receiver longitudinal axis, the retainer nesting in the distally facing recess, wherein, when the shank head enters into the central cavity via the distal opening and is increasingly proximally displaced against the retainer, the shank head increasingly radially expands the retainer until the hemisphere diameter reaches the retainer, the radial expansion of the retainer radially expanding the positioner, and wherein, upon the shank head hemisphere diameter proximally passing the retainer, the retainer radially self-contracts, ceases nesting in the distally facing recess, and moves distally away from the distally facing recess and along the shank head within the central cavity to reach a location in the central cavity that secures the retainer below the shank head hemisphere diameter when the shank longitudinal axis is aligned with the receiver longitudinal axis, so as to capture and prevent the shank head from distally exiting the central cavity via the distal opening.

15. The bone anchor assembly of claim 14, wherein the receiver central cavity includes an expansion chamber located between the channel and the distal opening, and the positioner is located within the expansion chamber and radially expandable about the receiver longitudinal axis into the expansion chamber.

16. The bone anchor assembly of claim 15, wherein the expansion chamber defines a circumferential recess in an interior wall surface of the receiver central cavity.

17. The bone anchor assembly of claim 15, wherein the shank head radially expanding the retainer drives the retainer into the positioner to radially expand the positioner into the expansion chamber.

18. The bone anchor assembly of claim 17, wherein the shank is cannulated.

19. The bone anchor assembly of claim 14, wherein the positioner further comprises an open ring shape having a gap such that the positioner is circumferentially discontinuous, the positioner gap allowing for the positioner to be compressible and expandable about a neutral position.

20. The bone anchor assembly of claim 19, wherein the positioner, in a compressed configuration, is configured for uploading into the receiver central cavity through the distal opening.

21. The bone anchor assembly of claim 14, wherein the positioner further includes a ringed distal lip defining a distal boundary of the distally facing recess and projecting radially inward, the retainer being located above the ringed distal lip when the retainer is nested in the distally facing recess.

22. The bone anchor assembly of claim 14, wherein the retainer further comprises an open ring shape having a gap such that the retainer is circumferentially discontinuous, the retainer gap allowing for the retainer to be compressible and expandable about a neutral position.

23. The bone anchor assembly of claim 22, wherein the retainer, in a compressed configuration, is configured for uploading into the receiver central cavity through the distal opening.

24. The bone anchor assembly of claim 14, wherein the location in the receiver central cavity reached by the retainer that secures the retainer below the shank head hemisphere diameter further comprises a proximally facing step surface radially extending from the distal opening.

25. The bone anchor assembly of claim 22, wherein the retainer nests against the proximally facing step in preventing the shank head from distally exiting the receiver central cavity via the distal opening.

26. The bone anchor assembly of claim 14, wherein the retainer does not tilt relative to the receiver longitudinal axis when the shank head pivots relative to the receiver.

27. The bone anchor assembly of claim 14, further comprising an insert positionable within the receiver after the positioner and the retainer and before the shank head.

28. The bone anchor assembly of claim 27, wherein an interference fit between an outer surface of the insert and an inner surface of the receiver maintains the insert in the receiver central cavity.

29. The bone anchor assembly of claim 28, wherein the interference fit is a male/female interference arrangement between an outer surface of the insert and an inner surface of the receiver.

30. The bone anchor assembly of claim 28, wherein the insert is downwardly deployable with a tool after the shank head is captured in the receiver central cavity by the retainer.

31. The bone anchor assembly of claim 28, wherein after the shank head is captured in the receiver central cavity, the interference fit inhibits the shank head from moving proximally within the receiver central cavity.

32. The bone anchor assembly of claim 27, wherein the insert is uploadable into the receiver through the distal opening prior to the positioner and the retainer.

* * * * *